(12) United States Patent
Mani et al.

(10) Patent No.: US 8,669,260 B2
(45) Date of Patent: Mar. 11, 2014

(54) KETOCONAZOLE-DERIVATIVE ANTAGONIST OF HUMAN PREGNANE X RECEPTOR AND USES THEREOF

(75) Inventors: Sridhar Mani, Riverdale, NY (US); Bhaskar C. Das, West Nyack, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 216 days.

(21) Appl. No.: 12/735,368

(22) PCT Filed: Jan. 27, 2009

(86) PCT No.: PCT/US2009/000524
§ 371 (c)(1),
(2), (4) Date: Jan. 13, 2011

(87) PCT Pub. No.: WO2009/110955
PCT Pub. Date: Sep. 11, 2009

(65) Prior Publication Data
US 2011/0105522 A1 May 5, 2011

Related U.S. Application Data

(60) Provisional application No. 61/067,688, filed on Feb. 29, 2008.

(51) Int. Cl.
*A61K 31/496* (2006.01)
*C07D 317/22* (2006.01)
(52) U.S. Cl.
USPC ........ 514/254.1; 544/374; 544/152; 548/517; 549/453
(58) Field of Classification Search
None
See application file for complete search history.

(56) References Cited

U.S. PATENT DOCUMENTS

| | | | |
|---|---|---|---|
| 4,590,282 A | 5/1986 | Henrick | |
| 5,495,052 A | 2/1996 | Shum et al. | |
| 6,376,514 B1 | 4/2002 | Degenhardt et al. | |
| 6,630,475 B2 | 10/2003 | Neustadt et al. | |

FOREIGN PATENT DOCUMENTS

WO WO 2007/078615 A2 7/2007

OTHER PUBLICATIONS

Power et al. Bioorganic & Medicinal Chemistry letters vol. 16, p. 887-890 (2006).*
Fotakis et al. Toxicology letters, vol. 160, pp. 171-177 (2006).*
Marques-Gallego et al. BMC Biotechnology, vol. 10, pp. 1-7 (2010).*
PCT Notification Concerning Transmittal of International Preliminary Report on Patentability and Written Opinion of the International Searching Authority in connection with PCT International Patent Application No. PCT/US2009/000524, 8 pages, (Mailed Sep. 10, 2010).
Ekins S et al., entitled "Human Pregnane X Receptor Antagonists and Agonists Define Molecular Requirements for Different Binding Sites," Mol Pharmacol 72:592-603, 2007.
Biswas A et al., entitled "Acetylation of Pregnane X Receptor protein determines selective function independent of ligand activation," Biochem Biophys Res Commun., Mar. 18, 2011;406(3):371-376.
Das B C, et al., entitled "Synthesis of novel ketoconazole derivatives as inhibitors of the human Pregnane X Receptor (PXR;NR1I2; also termed SXR, PAR)," Bioorganic & Medicinal Chemistry Letters, 18 (2008) 3974-3977.
Pondugula S R et al., entitled "Pregnane xenobiotic receptor in cancer pathogenesis and therapeutic response," Cancer Letters, 328 (2013), 1-9.
Venkatesh M, et al., entitled "In Vivo and In Vitro Characterization of First-in-Class Novel Azole Analog That Targets Pregnane X Receptor Activation," Mol Pharmacol, 80:124-135, 2011.
Wang H, et al., entitled "Pregnane X receptor activation induces FGF19-dependent tumor aggressiveness in humans and mice," J Clin Invest doi:10.1172/JCI41514. Epub Jul. 11, 2011.

* cited by examiner

*Primary Examiner* — Emily Bernhardt
(74) *Attorney, Agent, or Firm* — Amster, Rothstein & Ebenstein LLP

(57) ABSTRACT

The application discloses ketoconazole derivatives that are antagonists of the human pregnane X receptor (PXR), methods of preparing the derivatives, uses of the derivatives with drug therapy, and methods of inhibiting tumor cell proliferation and multidrug resistance using inhibitors of PXR.

14 Claims, 16 Drawing Sheets

A 1-(4-(4-(((2R,4S)-2-(2,4-difluorophenyl)
-2-methyl-1,3-dioxolan-4-yl)methoxy)phenyl)piperazin-1-yl)ethanone

B 1-(4-(4-(((2R,4S)-2-(2,4-dichlorophenyl)-2-methyl-1,3-dioxolan-4-
yl)methoxy)phenyl)piperazin-1-yl)ethanone

C 1-(4-(4-(((2R,4S)-2-((1H-imidazol-1-yl)methyl)-2-(2,4-dichlorophenyl)-
1,3-dioxolan-4-yl)methoxy)phenyl)piperazin-1-yl)ethanone

A

B

C

D

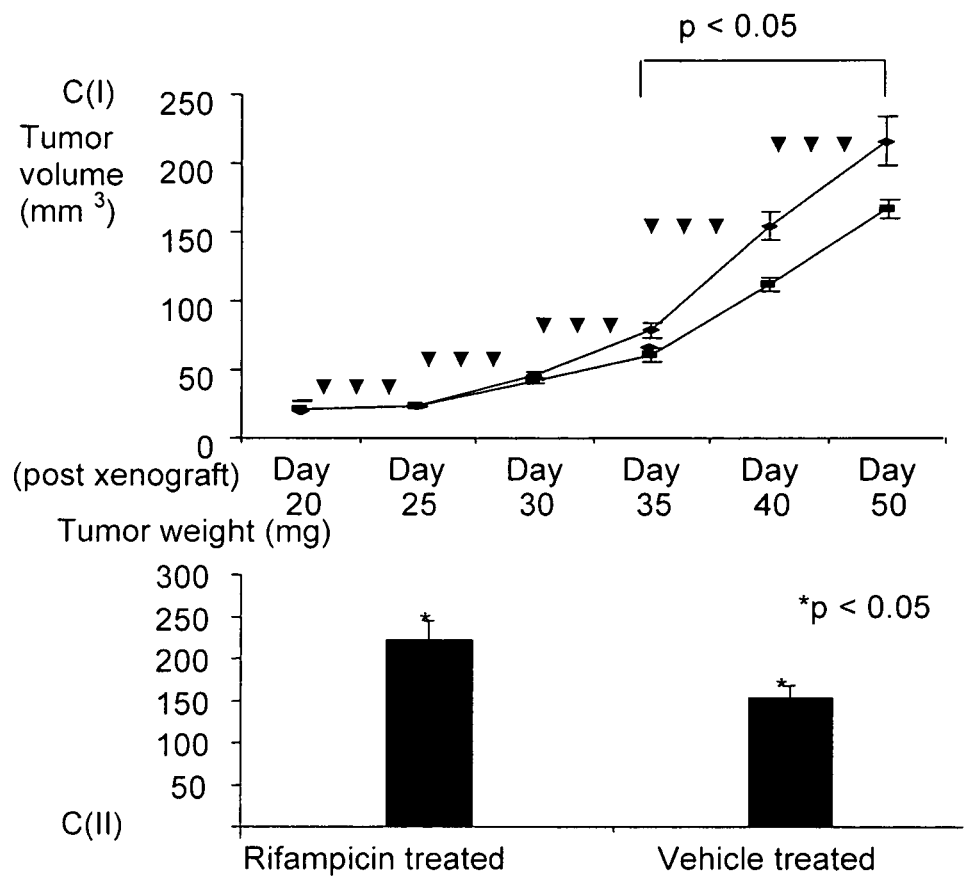
FIGURE 8C(I)-8C(II)

SEQUENCE LISTING

```
<160> NUMBER OF SEQ ID NOS: 16

<210> SEQ ID NO 1
<211> LENGTH: 18
<212> TYPE: DNA
<213> ORGANISM: artificial
<220> FEATURE:
<223> OTHER INFORMATION: forward primer sequence for PXR

<400> SEQUENCE: 1
gagctgatgg acgctcag                                                 18

<210> SEQ ID NO 2
<211> LENGTH: 18
<212> TYPE: DNA
<213> ORGANISM: artificial
```

```
<220> FEATURE:
<223> OTHER INFORMATION: reverse primer sequence for PXR

<400> SEQUENCE: 2
tggcaaagct gatgatgc                                                   18

<210> SEQ ID NO 3
<211> LENGTH: 19
<212> TYPE: DNA
<213> ORGANISM: artificial
<220> FEATURE:
<223> OTHER INFORMATION: forward primer sequence for GAPDH

<400> SEQUENCE: 3
tgcatcctgc accaccaac                                                  19

<210> SEQ ID NO 4
<211> LENGTH: 19
<212> TYPE: DNA
<213> ORGANISM: artificial
<220> FEATURE:
<223> OTHER INFORMATION: reverse primer sequence for GAPDH

<400> SEQUENCE: 4
cgcctgcttc accaccttc                                                  19

<210> SEQ ID NO 5
<211> LENGTH: 22
<212> TYPE: DNA
<213> ORGANISM: artificial
<220> FEATURE:
<223> OTHER INFORMATION: forward primer sequence for CYP3A4

<400> SEQUENCE: 5
tggtgaatga aacgctcaga tt                                              22

<210> SEQ ID NO 6
<211> LENGTH: 23
<212> TYPE: DNA
<213> ORGANISM: artificial
<220> FEATURE:
<223> OTHER INFORMATION: reverse primer sequence for CYP3A4

<400> SEQUENCE: 6
catctttttt gcagaccctc tca                                             23

<210> SEQ ID NO 7
<211> LENGTH: 19
<212> TYPE: DNA
<213> ORGANISM: artificial
<220> FEATURE:
<223> OTHER INFORMATION: CYP3A4 probe sequence

<400> SEQUENCE: 7
ttcccaattg ctatgagac                                                  19

<210> SEQ ID NO 8
<211> LENGTH: 20
<212> TYPE: DNA
<213> ORGANISM: artificial
<220> FEATURE:
<223> OTHER INFORMATION: forward primer sequence for CYP2B6

<400> SEQUENCE: 8
gaccgagcca aaatgccata                                                 20
```

```
<210> SEQ ID NO 9
<211> LENGTH: 23
<212> TYPE: DNA
<213> ORGANISM: artificial
<220> FEATURE:
<223> OTHER INFORMATION: reverse primer sequence for CYP2B6

<400> SEQUENCE: 9
ggtcggaaaa tctctgaatc tca                                             23

<210> SEQ ID NO 10
<211> LENGTH: 15
<212> TYPE: DNA
<213> ORGANISM: artificial
<220> FEATURE:
<223> OTHER INFORMATION: CYP2B6 probe sequence

<400> SEQUENCE: 10
acagaggcag tcatc                                                      15

<210> SEQ ID NO 11
<211> LENGTH: 23
<212> TYPE: DNA
<213> ORGANISM: artificial
<220> FEATURE:
<223> OTHER INFORMATION: forward primer sequence for MDR-1

<400> SEQUENCE: 11
ggaagccaat gcctatgact tta                                             23

<210> SEQ ID NO 12
<211> LENGTH: 20
<212> TYPE: DNA
<213> ORGANISM: artificial
<220> FEATURE:
<223> OTHER INFORMATION: reverse primer sequence for MDR-1

<400> SEQUENCE: 12
actcaactgg gcccctctct                                                 20

<210> SEQ ID NO 13
<211> LENGTH: 31
<212> TYPE: DNA
<213> ORGANISM: artificial
<220> FEATURE:
<223> OTHER INFORMATION: MDR-1 probe sequence

<400> SEQUENCE: 13
catgaaactg cctcataaat ttgacaccct g                                    31

<210> SEQ ID NO 14
<211> LENGTH: 23
<212> TYPE: DNA
<213> ORGANISM: artificial
<220> FEATURE:
<223> OTHER INFORMATION: forward primer sequence for MRP-2

<400> SEQUENCE: 14
ggctgttgag cgataactg agt                                              23

<210> SEQ ID NO 15
<211> LENGTH: 17
<212> TYPE: DNA
<213> ORGANISM: artificial
<220> FEATURE:
<223> OTHER INFORMATION: reverse primer sequence for MRP-2
```

```
<400> SEQUENCE: 15
gcctttgctg ggccaat                                                    17

<210> SEQ ID NO 16
<211> LENGTH: 30
<212> TYPE: DNA
<213> ORGANISM: artificial
<220> FEATURE:
<223> OTHER INFORMATION: MRP-2 probe sequence

<400> SEQUENCE: 16
aaaatgaggc accctgggtg actgataaga                                      30
```

KETOCONAZOLE-DERIVATIVE ANTAGONIST OF HUMAN PREGNANE X RECEPTOR AND USES THEREOF

CROSS-REFERENCE TO RELATED APPLICATIONS

This application is a national stage entry under 35 U.S.C. §371 of PCT International Patent Application No. PCT/US2009/000524, filed Jan. 27, 2009, and claims priority to U.S. Provisional Patent Application No. 61/067,688, filed Feb. 29, 2008, the contents of which are incorporated herein by reference in their entirety into the subject application.

FIELD OF THE INVENTION

The present invention relates to ketoconazole derivatives that are antagonists of the human pregnane X receptor (PXR), methods of preparing the derivatives, uses of the derivatives with drug therapy, and methods of inhibiting tumor cell proliferation and multidrug resistance using inhibitors of PXR.

BACKGROUND OF THE INVENTION

Throughout this application various publications are referred to in parenthesis. Citations for these references may be found at the end of the specification immediately preceding the claims. The disclosures of these publications are hereby incorporated by reference in their entireties into the subject application to more fully describe the art to which the subject application pertains.

Pregnane X Receptor (PXR) (NR1I2; also termed SXR, PAR) is the primary xenobiotic sensor in human and mammalian tissues. It responds to a wide range of structurally- and chemically-distinct ligands that range from small lipophilic drugs (e.g., rifampicin) to potentially toxic bile acids as well as cholesterol metabolites (1-10, 31). A large number of commonly encountered environmental toxins (e.g., phthalates), chemotherapy (e.g., taxanes), drug vehicles (e.g., DEHP), co-medications (e.g., dexamethasone), and herbals (e.g., curcumin, hyperforin) can activate PXR. To date, only three PXR antagonist have been described: ketoconazole (and related azoles; 11), suphoraphane (12) and ecteinascidin-743 (ET-743) (13). Ketoconazole was first described as a PXR antagonist by Takeshita et al. (14), and was subsequently shown to disrupt the binding of coregulators (including both coactivators and corepressors) to the surface of PXR in an agonist-dependent fashion (15). In the presence of the established PXR activator rifampicin, ketoconazole and related azoles were shown to prevent the activation of the receptor both in cell-based assays as well as in a humanized PXR mouse model (16). Ketoconazole binds to at least a region outside the ligand-binding pocket. The revertant activation function 2 (AF-2) region double mutant of PXR (T248E/K277Q) activates with rifampicin but is not inhibited by ketoconazole (11, 17).

The promiscuous activation of PXR by natural substances and xenobiotics has been implicated as a mechanism that accelerates the metabolism of affected drugs, which leads to unanticipated adverse drug reactions and lack of efficacy. PXR activation in the gut can lower drug bioavailability. Recent data also supports a major role for PXR activation in controlling (decreasing) the transport of drugs across blood brain barrier (32), underscoring PXR's role in drug delivery to the brain and limiting the effectiveness of therapeutics on primary brain tumors or brain metastases. Therefore, in the context of cancer therapeutics, controlling PXR activation serves to improve both drug metabolism and delivery. Thus, there is a need for new, non-toxic antagonists of PXR activation as well as a further understanding of how PXR inhibition can benefit treatment of diseases such as cancer.

SUMMARY OF THE INVENTION

The present invention is directed to ketoconazole derivatives having the formula:

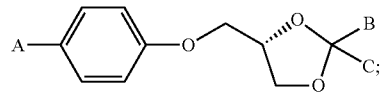

wherein A, B and C are defined herein below.

The invention also provides a method of preparing a compound of formula (3)

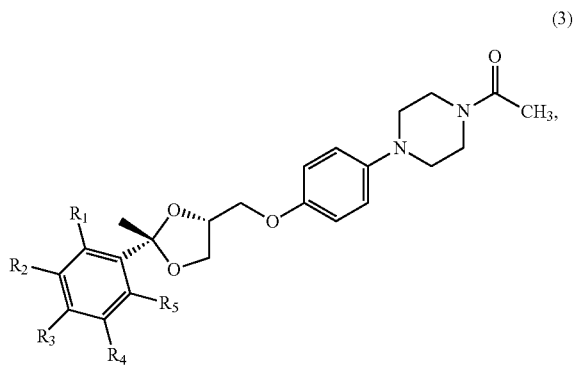

the method comprising:
(a) reacting (S)-(−)-glycidol and 4-bromophenol in the presence of a mild base and dimethylformamide (DMF) to produce a compound of formula (1)

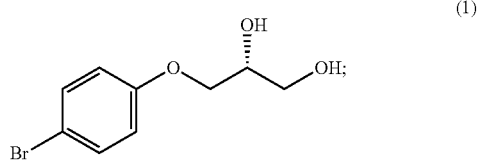 [SMILES: OC[C@@H](O)COc1ccc(Br)cc1]

(b) reacting the compound of formula (1) with an acetophenone derivative in the presence of p-toluenesulfonic acid monohydrate and either benzene or toluene to produce a compound of formula (2)

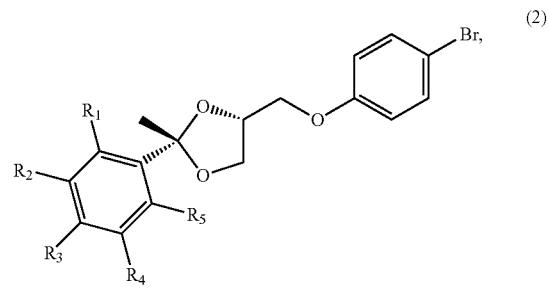

wherein each $R_1$, $R_2$, $R_3$, $R_4$ and $R_5$ is independently H, F, Cl, Br, I, $OCH_3$, $OC_2H_5$, O-alkyl, SH, S-alkyl, $NH_2$, NH-alkyl, alkyl, phenyl or heterocyclic; and (c) reacting the compound of formula (2) with 1-acetylpiperazine in the presence of a palladium catalyst or a copper catalyst to produce the compound of formula (3).

The invention further provides methods of preventing or reducing proliferation of tumor cells and methods of preventing or reducing multidrug resistance in tumor cells, where the methods comprise contacting the tumor cells with an inhibitor of the human pregnane X receptor (PXR).

The invention also provides pharmaceutical compositions for antagonizing the human pregnane X receptor (PXR) comprising a compound of the present invention and a pharmaceutically acceptable carrier or diluent.

The invention also provides a method of inhibiting the human pregnane X receptor (PXR) in a subject comprising administering to the subject a compound of the present invention in an amount and manner effective to inhibit the human pregnane X receptor (PXR).

BRIEF DESCRIPTION OF THE DRAWINGS

FIG. 8A-8D. PXR activation in LS174T cells induces cell proliferation. (A) Doubling time of LS174T cells in the presence and absence of PXR agonist, rifampicin. * p<0.001, student t test. (B) Survival of LS174T cells (as in A), as determined using the MTT assay, in the presence and absence of rifampicin. Data shown as fold survival (values normalized to vehicle control). (C)(I), LS174T cells were grown as xenografts in 6-8 week old C57BL/6 mice (n=6 per treatment group; LS174T cells). On day 20, clinically palpable (~15-20 mm³) tumors on each flank were treated with rifampicin (ip, 3 days/week till day 50). Tumors were measured every other day and plotted in 5-day intervals. p<0.05 (2-way ANOVA). Vector transfected—rifampicin treated (-♦-); vector transfected—vehicle treated (—■—). (C)(II), On day 50, all animals were sacrificed and tumors excised and weighed. * p<0.3 and ** p<0.05, student t test. (D) Transwell migration assay determined at three time points, 5, 12 and 24 hrs in the presence or absence of rifampicin (25 μM) or EGF (5 nM) or both. Each assay was performed four separate times each in triplicate. The vehicle control for all experiments was 0.2% DMSO. Points or histogram, mean values; bars, SE.

DETAILED DESCRIPTION OF THE INVENTION

Figures 1A, 1B, 1C, 1D, 1E, 1F, 1G, 1H:
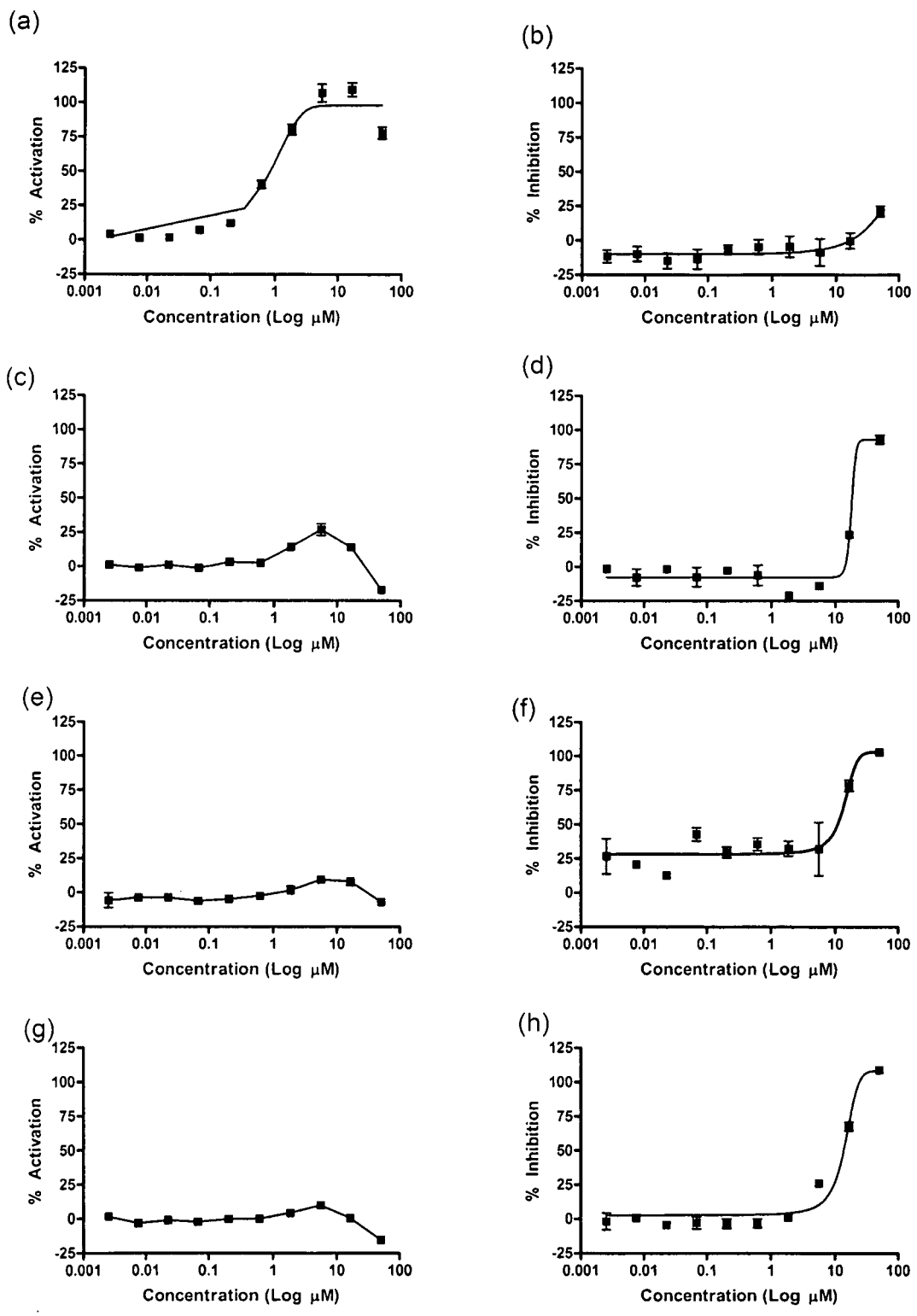
FIG. 1A-1H. Concentration-response curves for PXR activation with (a) rifampicin, (c) ketoconazole, (e) FL-B-12 and (g) UCL2158H. The concentration-response curves for activated PXR antagonism are shown with (b) rifampicin, (d) ketoconazole, (f) FL-B-12 and (h) UCL2158H.
Figure 2A:
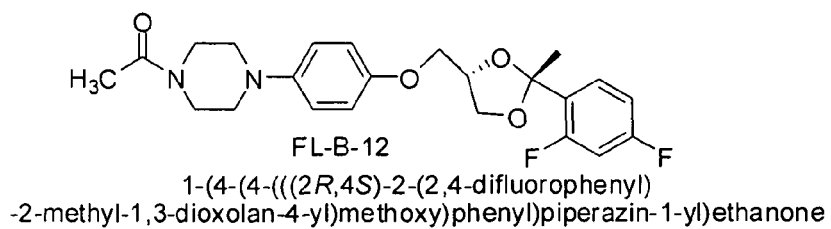
FIG. 2A-2C. Chemical 2D structures of (A) ketoconazole, (B) UCL2158H and (C) FL-B-12.
Figure 2B:
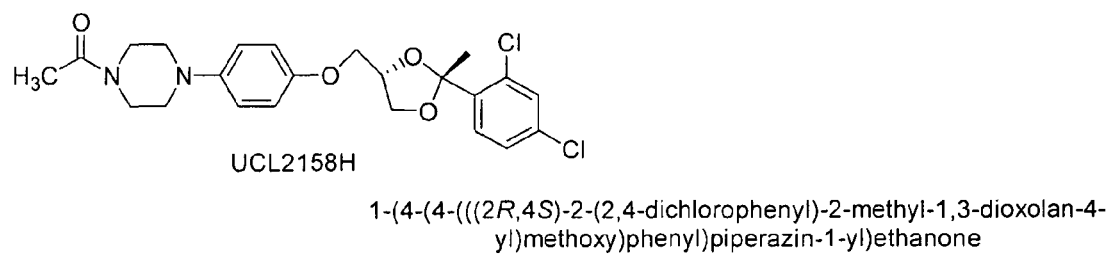
Figure 2C:
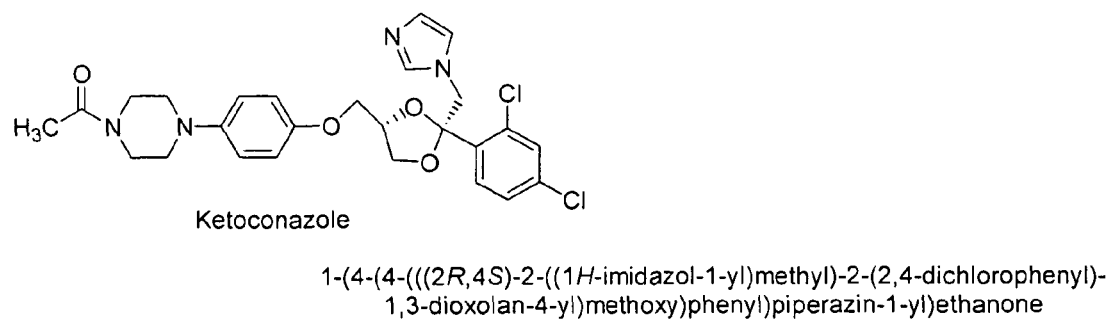
Figure 3A:
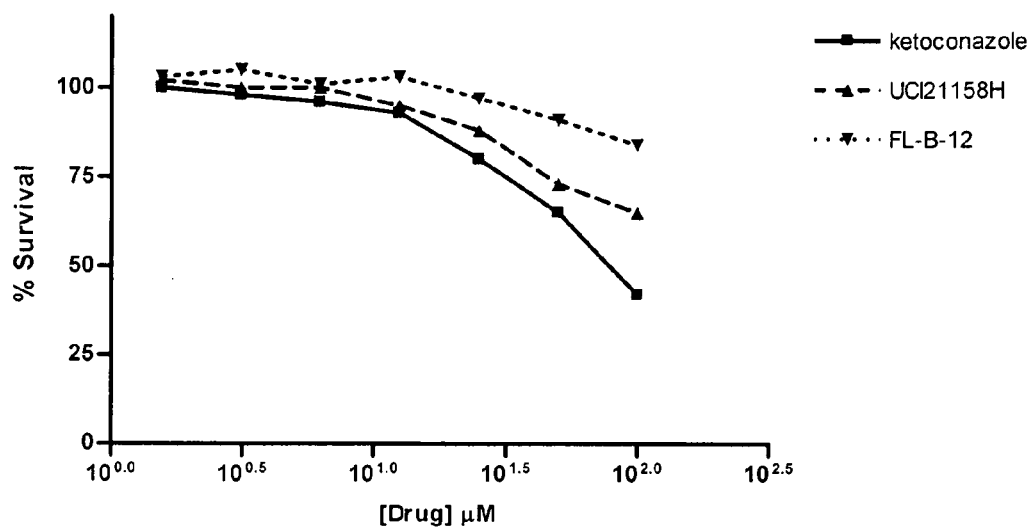
FIG. 3A-3D. Effect of ketoconazole, UCL2158H and FL-B-12 on cancer cell lines LS174T (A), Caco2 (B) and SKOV3 (C) as well as normal fibroblast cells CRL-2522 (D). Average of three independent experiments each performed in triplicate (n=3) (±) SD<0.01%. Ketoconazole (—■—), UCL2158H (-▲-) and FL-B-12 (-▼-).
Figure 3B:
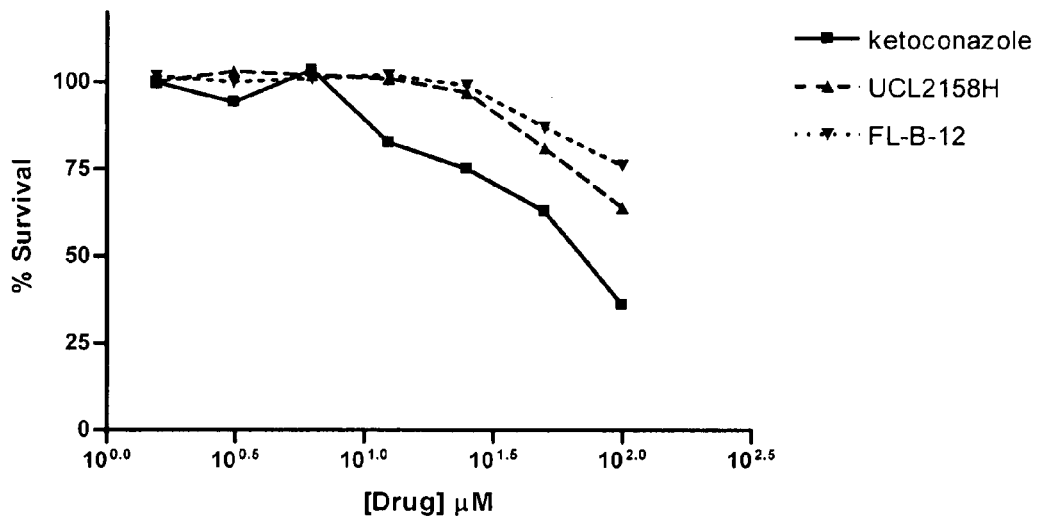
Figure 3C:
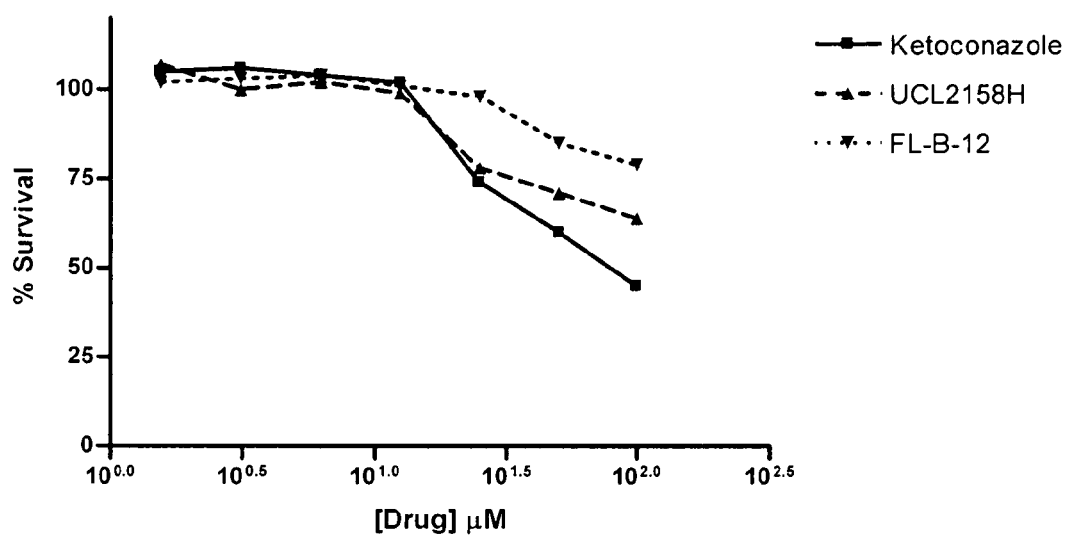
Figure 3D:
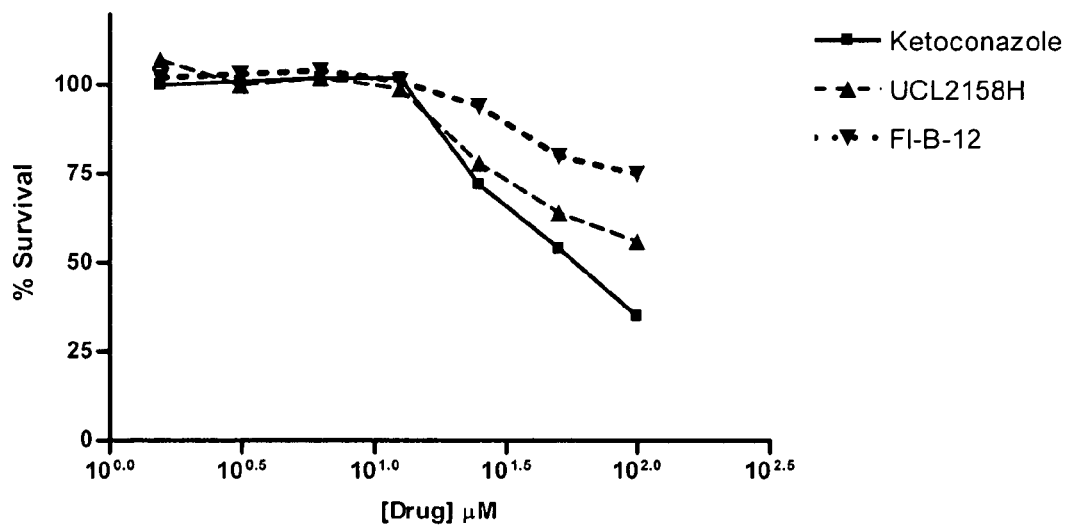

The invention provides a compound having the formula:

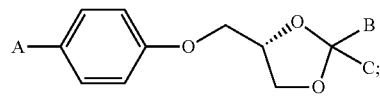

wherein A is

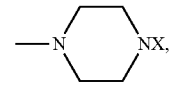

where X is H, CHO, COCH₃, CO—OCH₃, CO—OC₂H₅, CONH₂, CONHCH₃, CONHC₂H₅, CSNHCH₃, CH₂CH₃, COO—CH₃, COO—C₂H₅, CH₃, CH₂—CH(CH₃)₂, CO—NH—(CH$_2$)$_2$CH$_3$, CH(CH$_3$)$_2$, (CH$_2$)$_3$CH$_3$, (CH$_2$)$_2$CH$_3$, SO$_2$CH$_3$, CH$_2$C$_6$H$_5$, or SO$_2$CH$_2$C$_6$H$_5$; and wherein B and C are independently methyl, ethyl, propyl, butyl, CH$_2$(CH$_2$)$_n$CH$_2$CH$_3$ where n=0-10, cyclopropyl, cyclobutyl, cyclopentyl, cyclohexyl, cycloheptyl, a heterocyclic,

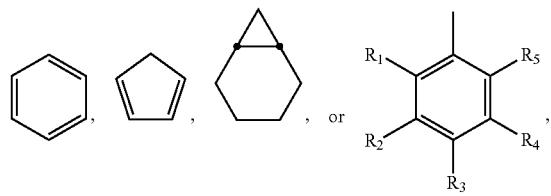

wherein each R$_1$, R$_2$, R$_3$, R$_4$ and R$_5$ is independently H, F, Cl, Br, I, OCH$_3$, OC$_2$H$_5$, O-alkyl, SH, S-alkyl, NH$_2$, NH-alkyl, alkyl, phenyl or heterocyclic;

or a pharmaceutically acceptable salt thereof;

with the proviso that the compound is not ketoconazole or 1-(4-(4-((2R,4S)-2-(2,4-dichlorophenyl)-2-methyl-1,3-dioxolan-4-yl)methoxy)phenyl)piperazin-1-yl)ethanone.

Preferably, X is H, CHO or COCH$_3$. Preferably, A is

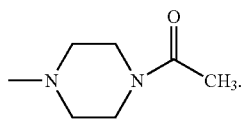

The invention also provides a compound having the formula:

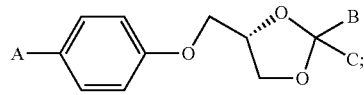

wherein A is —N=C=S; —N(CH$_3$)$_2$; or —NHD, where D is H, CHO, CS—NH$_2$, CS—NH—CH$_3$, CS—NH—C$_2$H$_5$, CH$_2$CH$_3$, or CH$_3$; or —NHCOE, where E is C$_2$H$_5$, OCH$_3$, OC$_2$H$_5$, NH—CH$_3$, NH—C$_2$H$_5$, CH(G)$_2$ where G is H, F, Cl, Br or I; or

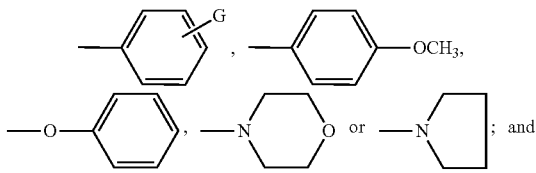

wherein B and C are independently methyl, ethyl, propyl, butyl, CH$_2$(CH$_2$)$_n$CH$_2$CH$_3$ where n=0-10, cyclopropyl, cyclobutyl, cyclopentyl, cyclohexyl, cycloheptyl, a heterocyclic,

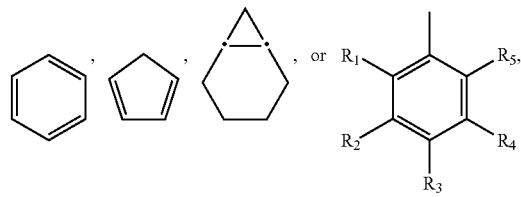

wherein each R$_1$, R$_2$, R$_3$, R$_4$ and R$_5$ is independently H, F, Cl, Br, I, OCH$_3$, OC$_2$H$_5$, O-alkyl, SH, S-alkyl, NH$_2$, NH-alkyl, alkyl, phenyl or heterocyclic; or a pharmaceutically acceptable salt thereof.

Preferred structures of variable A include:

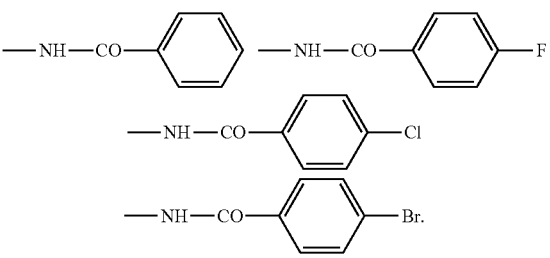

Preferably, B is CH$_3$.
Preferably, C is

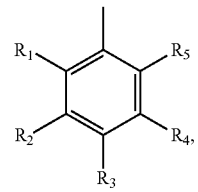

wherein each R$_1$, R$_2$, R$_3$, R$_4$ and R$_5$ is independently H, F, Cl, Br or I, or wherein each R$_1$, R$_2$, R$_3$, R$_4$ and R$_5$ is independently H, F, Br or I. Preferably, at least two of R$_1$, R$_2$, R$_3$, R$_4$ and R$_5$ are F, Br or I, and the remainder are H. Preferably, at least R$_3$ is F.

Examples of the structure of A include:

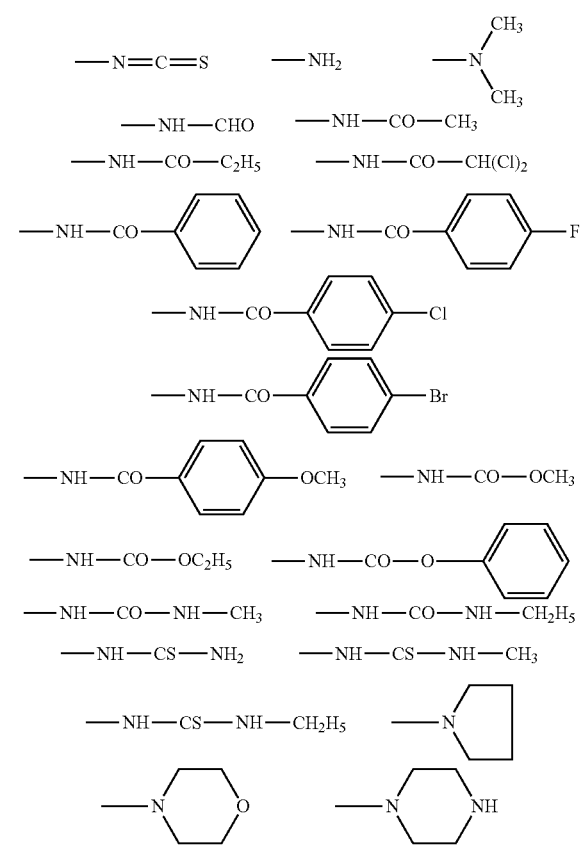

-continued
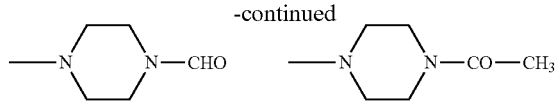
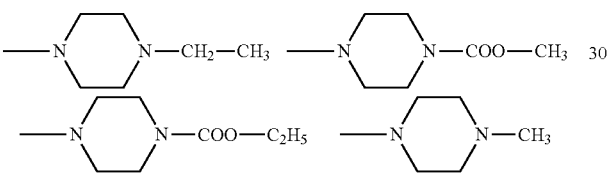
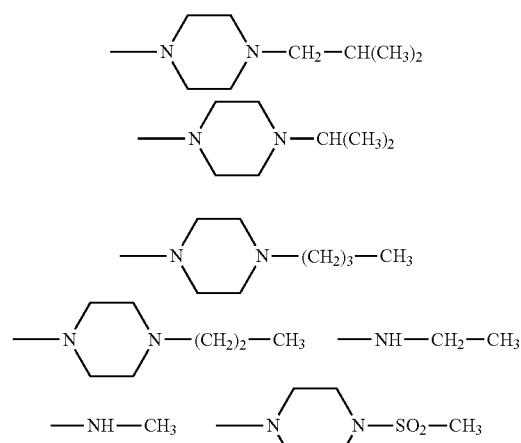
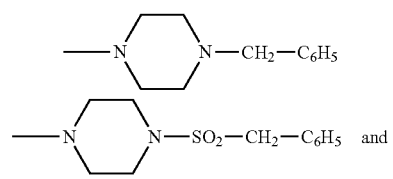
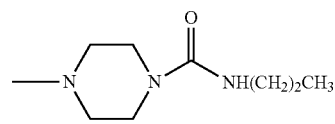
The compound can have a structure selected from the group consisting of:
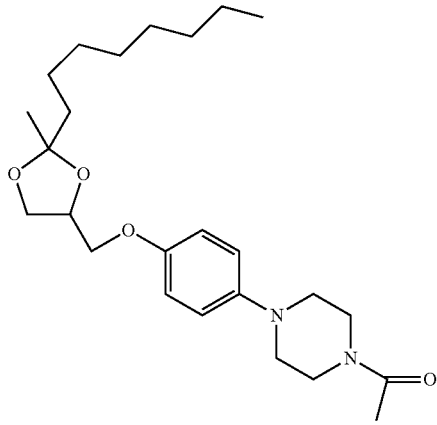
(1)
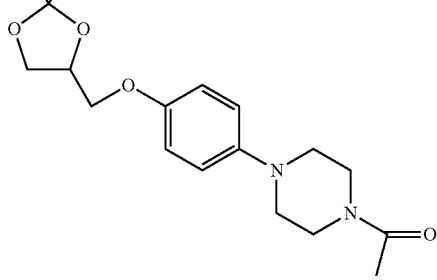
(2)
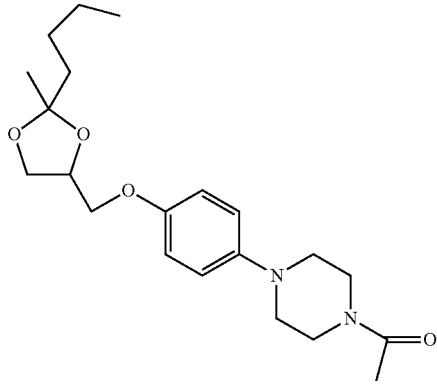
(3)
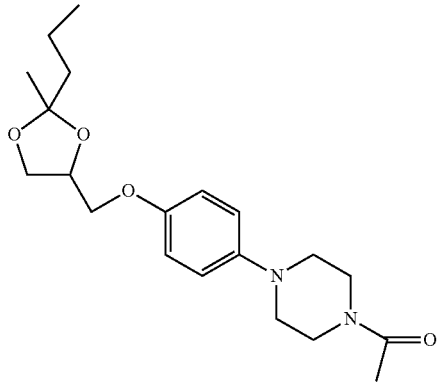
(4)

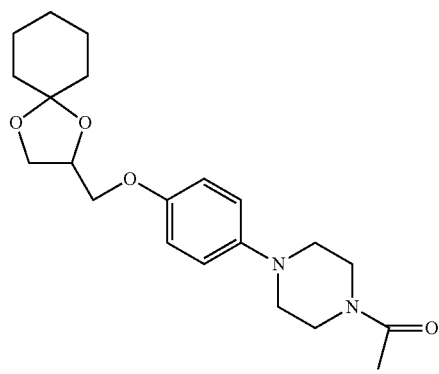
(5)
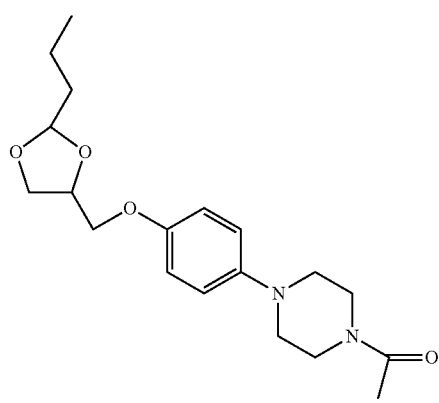
(6)
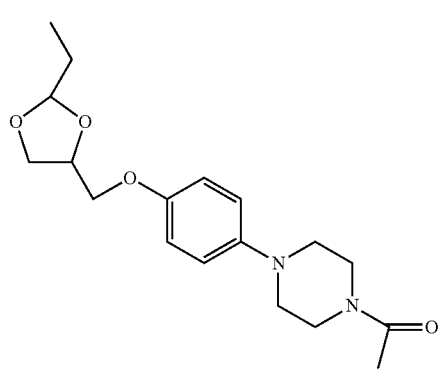
(7)
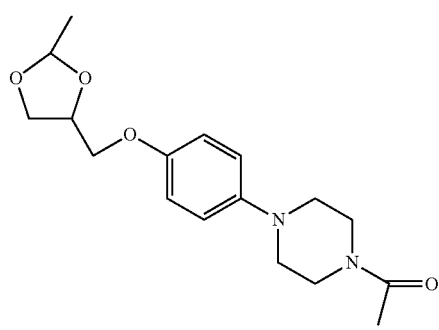
(8)
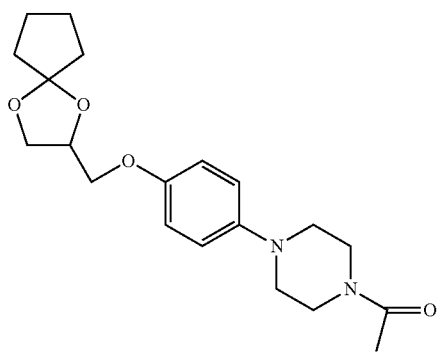
(9)
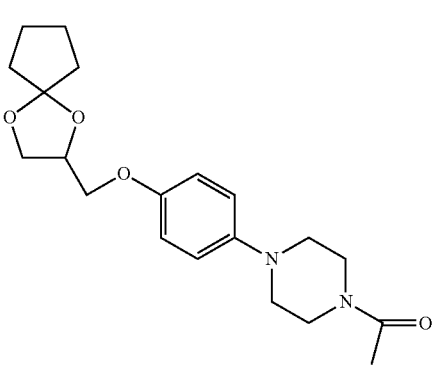
(10)
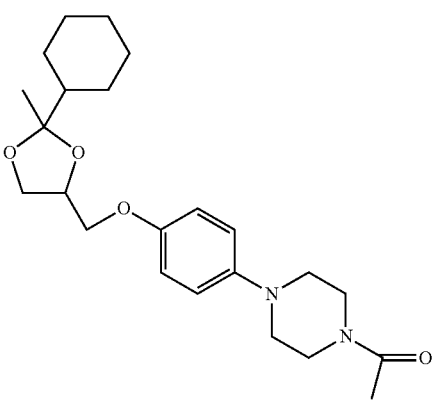
(11)
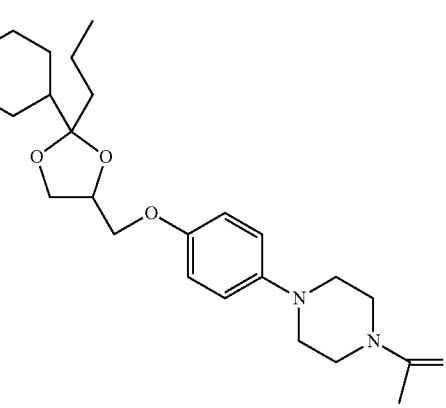
(12)

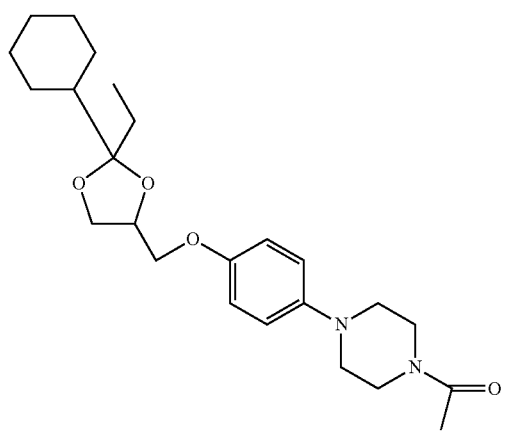
(13)
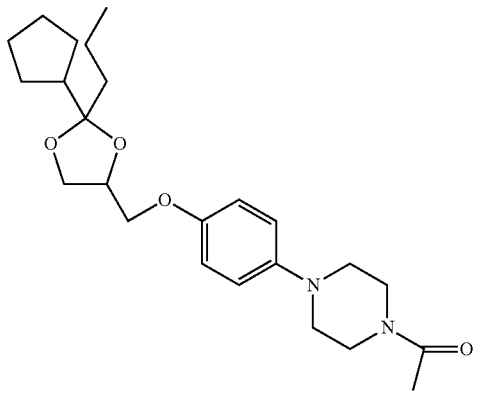
(17)
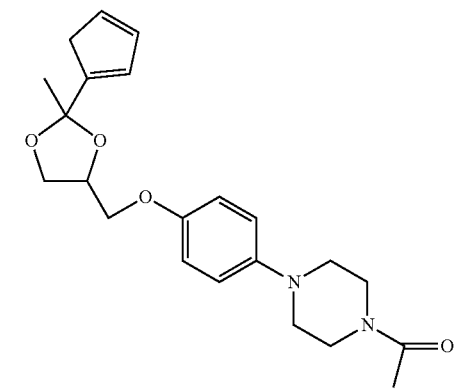
(14)
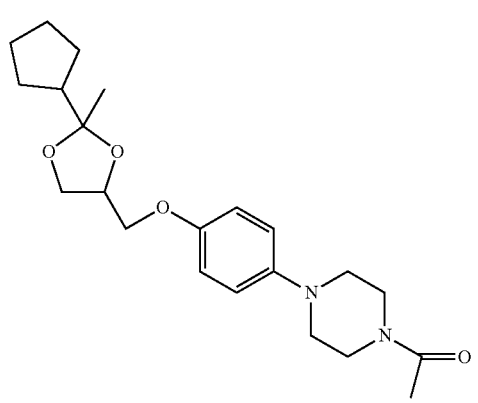
(17)
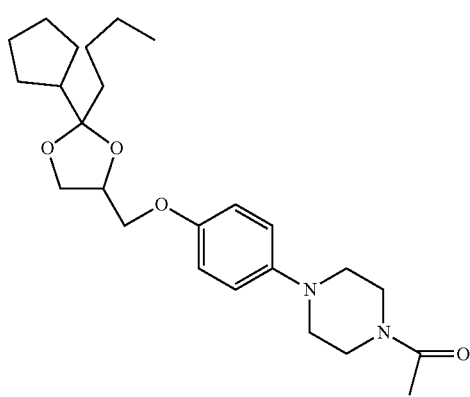
(15)
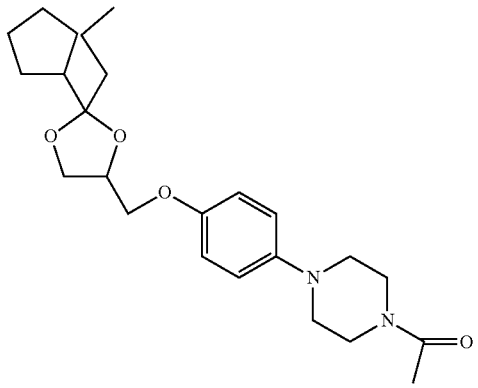
(18)
(16)
(19)

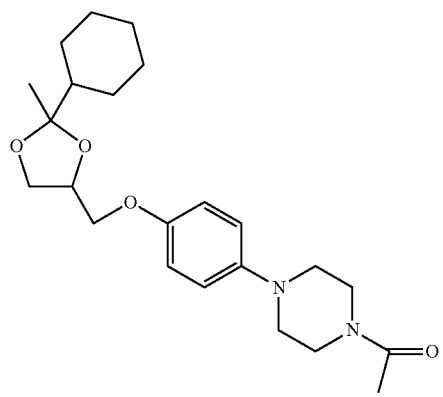
(20)
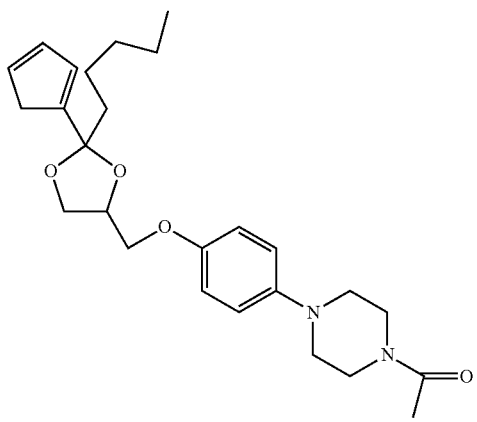
(24)
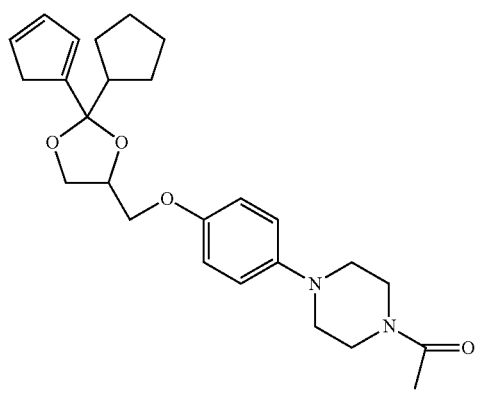
(21)
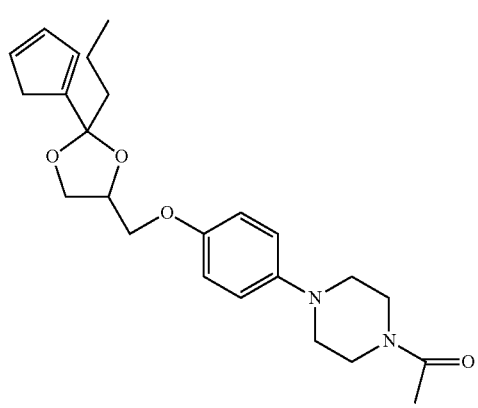
(22)
The compound can also have a structure selected from the group consisting of:
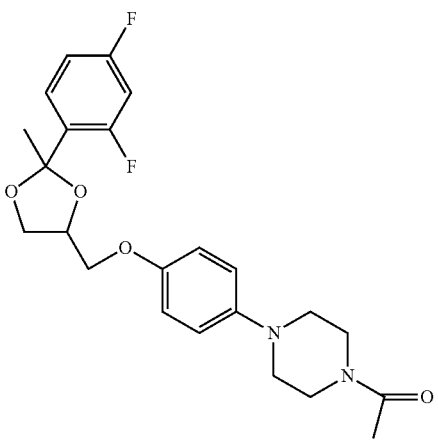
(1)
(2)

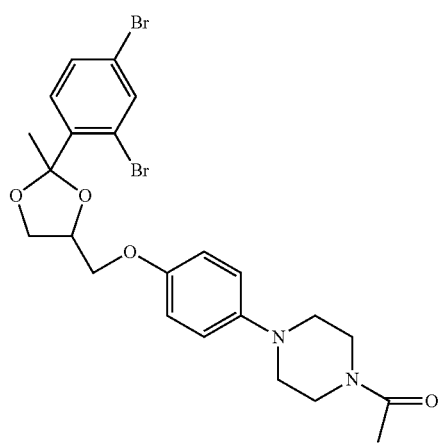
(3)
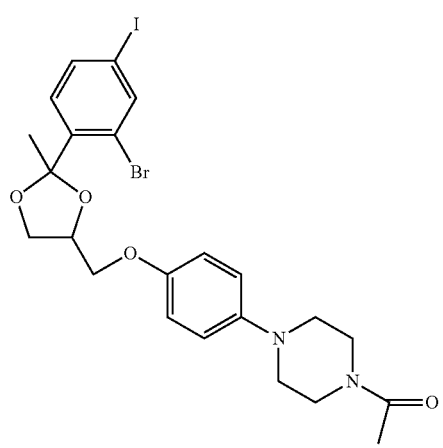
(6)
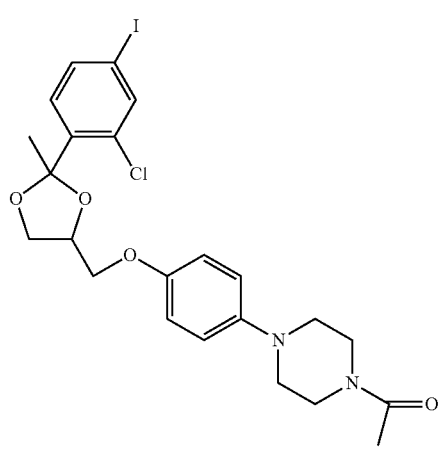
(4)
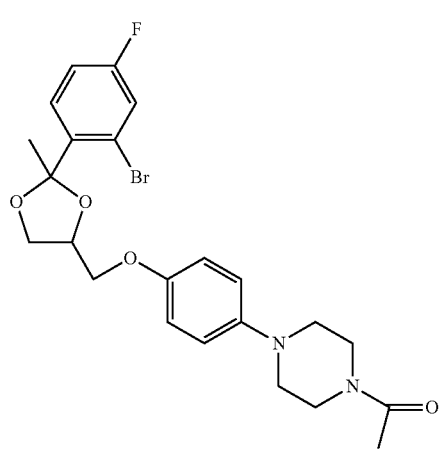
(7)
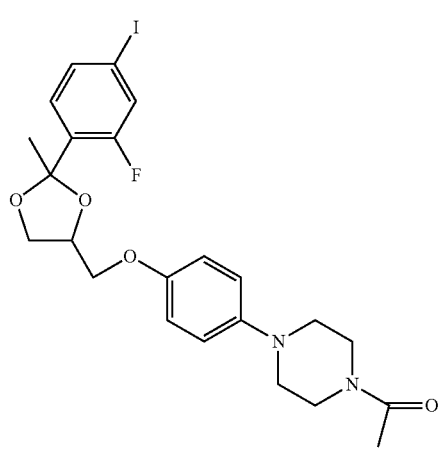
(5)
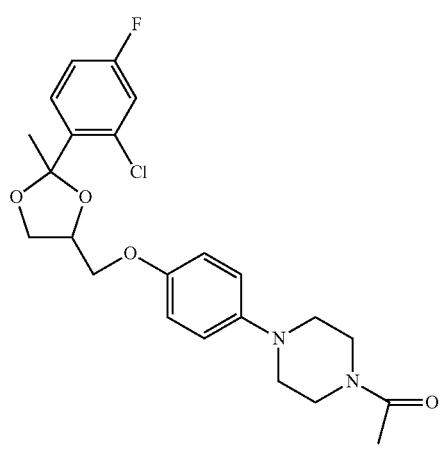
(8)

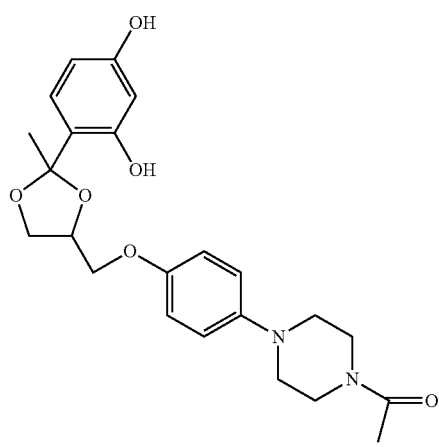
(9)
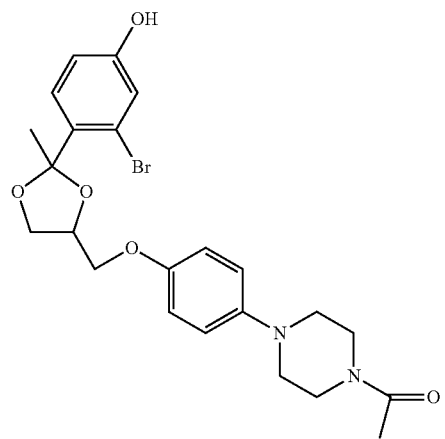
(12)
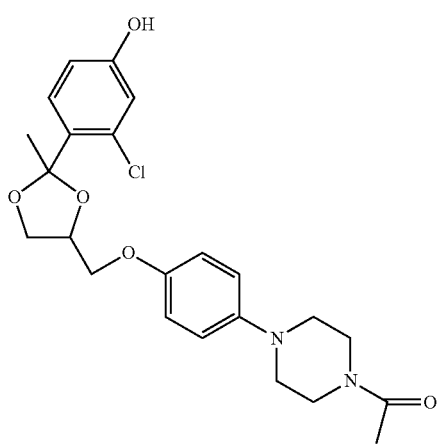
(10)
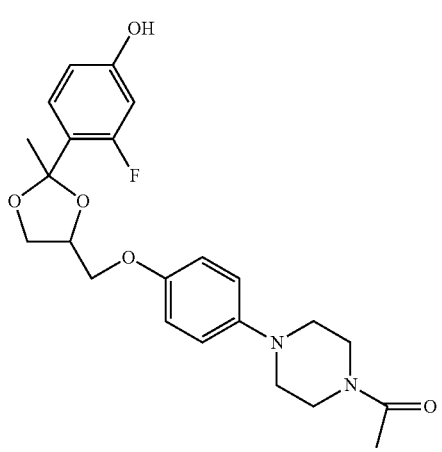
(11)
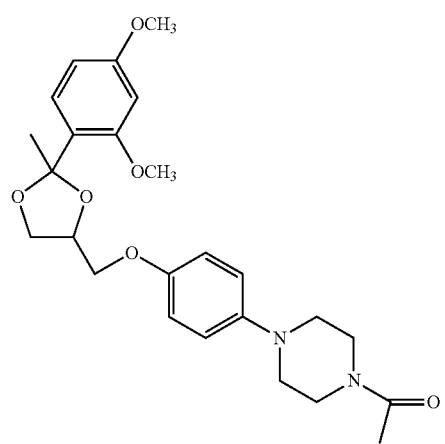
(13)
(14)

(15)
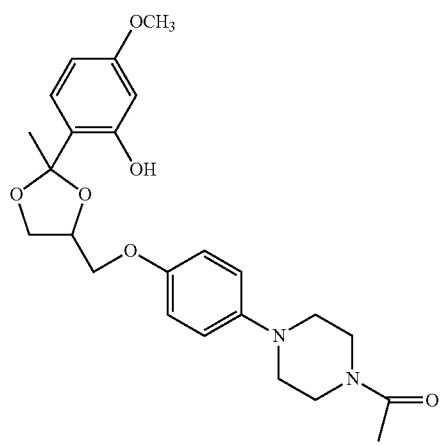
(16)
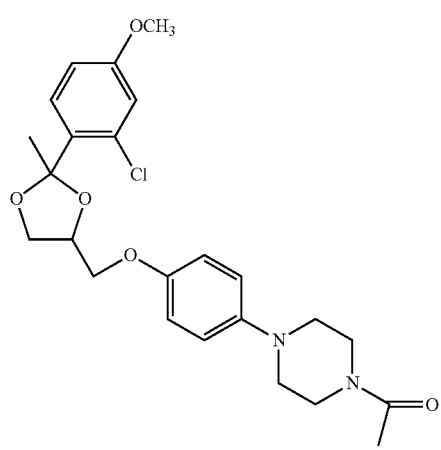
(17)
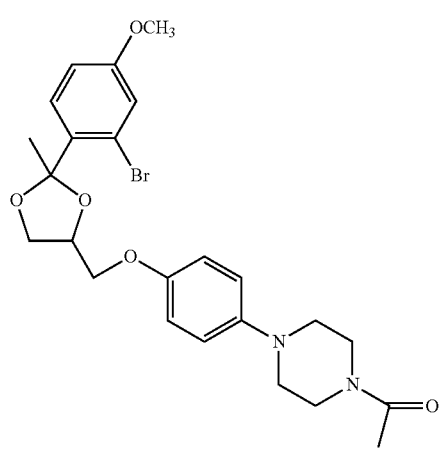
(18)
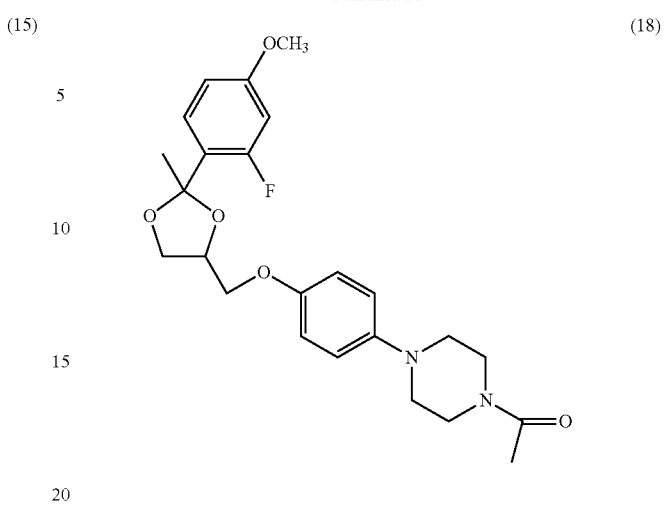
(19)
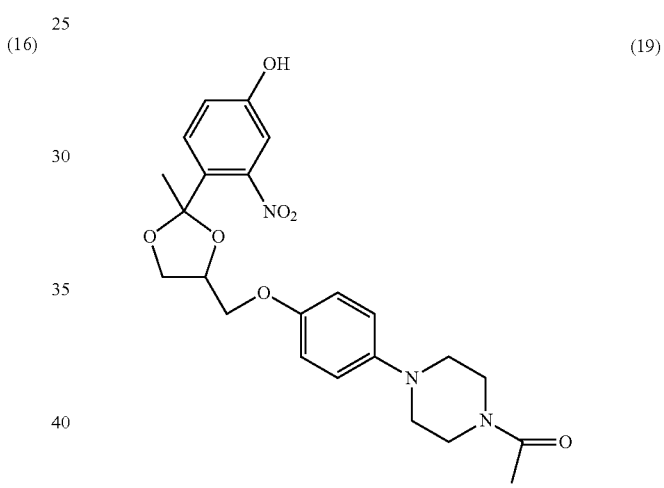
(20)
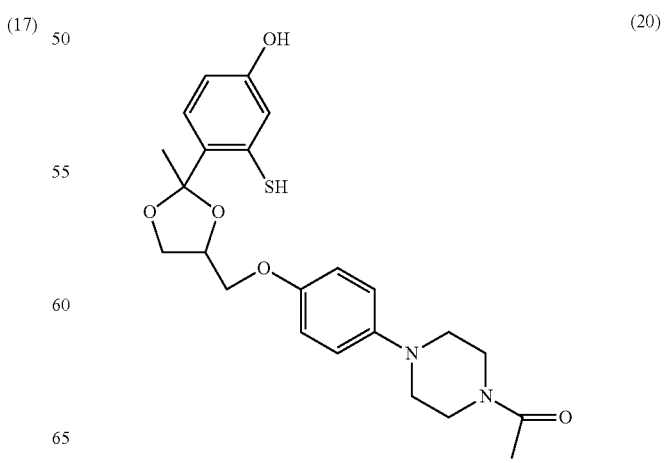

-continued
(21)
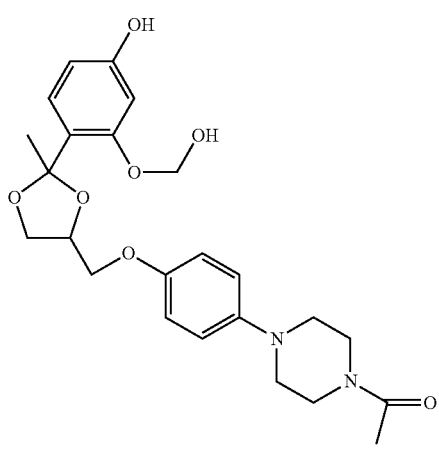
(22)
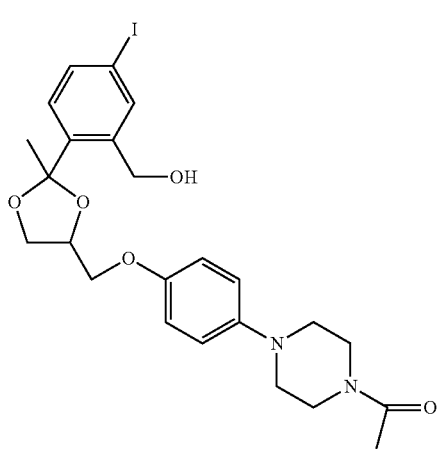
(23)
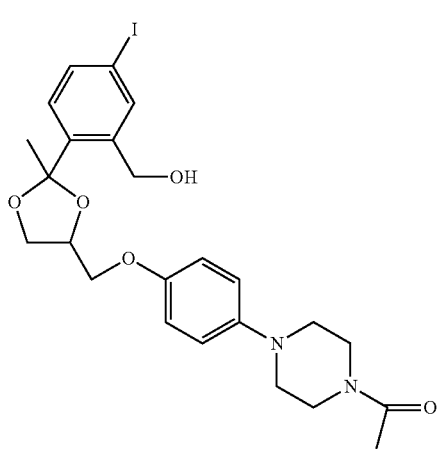
-continued
(24)
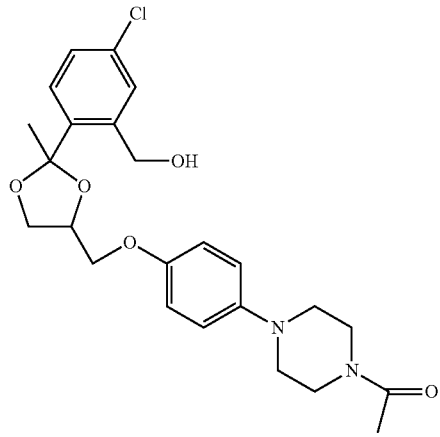
(25)
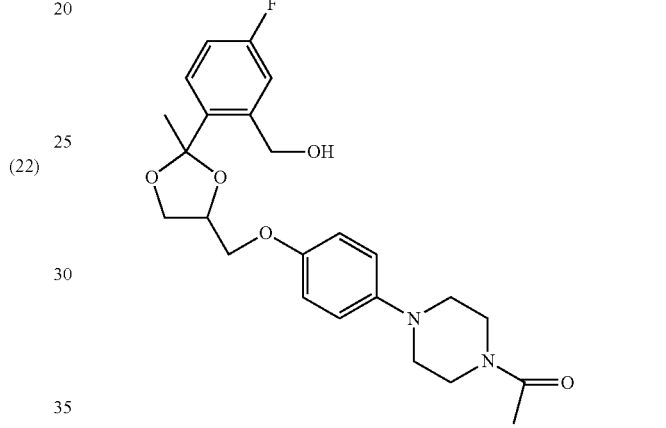
(26)
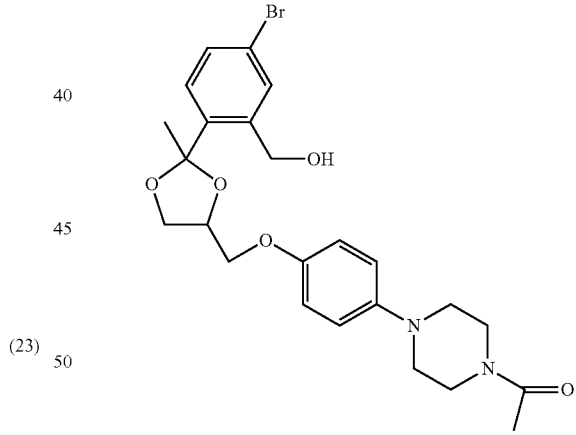
A preferred compound has the structure:
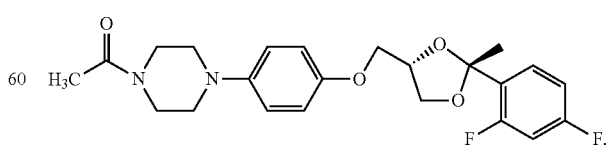
The compounds of the present invention exclude compounds UCL2112H, UCL2134D, UCL2135, UCL2202D, UCL2245 and UCL2238.

Pharmaceutically acceptable salts that can be used with compounds of the present invention are non-toxic salts derived for example from inorganic or organic acids including, but not limited to, salts derived from hydrochloric, sulfuric, phosphoric, acetic, lactic, fumaric, succinic, tartaric, gluconic, citric, methanesulphonic and p-toluenesulphonic acids.

The invention also provides a method of preparing a compound of formula (3)

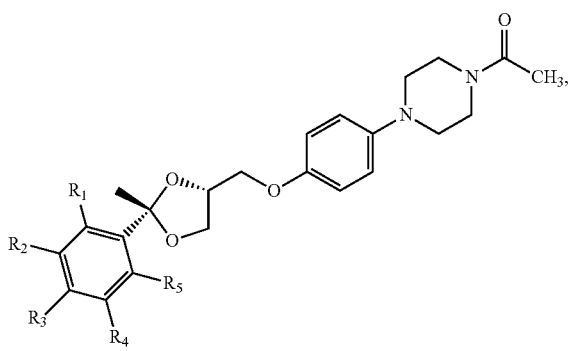

wherein each $R_1$, $R_2$, $R_3$, $R_4$ and $R_5$ is independently H, F, Cl, Br, I, $OCH_3$, $OC_2H_5$, O-alkyl, SH, S-alkyl, $NH_2$, NH-alkyl, alkyl, phenyl or heterocyclic. The method comprises three steps, steps (a), (b) and (c).

Step (a) comprises reacting (S)-(−)-glycidol and 4-bromophenol in the presence of a mild base and dimethyl formamide (DMF) to produce a compound of formula (1):

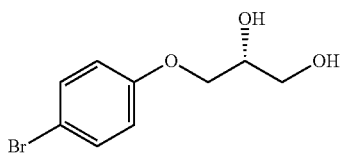 [SMILES: OC[C@@H](O)COc1ccc(Br)cc1]

Examples of mild bases that can be used include, but are not limited to, sodium carbonate, potassium carbonate, lithium carbonate, cesium carbonate, sodium hydride, potassium hydride, and lithium hydride. A preferred base is $K_2CO_3$. Preferably, the reaction is carried out between 100° C.-120° C. for 5-10 hours.

Step (b) comprises reacting the compound of formula (1) with an acetophenone derivative in the presence of p-toluenesulfonic acid monohydrate and either benzene or toluene to produce a compound of formula (2)

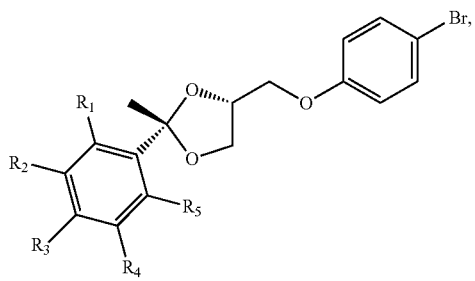

wherein each $R_1$, $R_2$, $R_3$, $R_4$ and $R_5$ is independently H, F, Cl, Br, I, $OCH_3$, $OC_2H_5$, O-alkyl, SH, S-alkyl, $NH_2$, NH-alkyl, alkyl, phenyl or heterocyclic. Preferably, the reaction is carried out at 100° C.-120° C. for 10-30 hours.

Step (c) comprises reacting the compound of formula (2) with 1-acetylpiperazine in the presence of a palladium catalyst or a copper catalyst to produce the compound of formula (3). Examples of catalysts that can be used include, but are not limited to, Pd(dba)$_2$, palladium carbonate, palladium acetate, copper acetate and copper carbonate. Preferably, the reaction is carried out between 80° C.-100° C. for 10-24 hours.

The invention further provides a compound prepared by the method of the present invention.

Preferably, the compounds of the present invention have reduced cytotoxicity compared to ketoconazole and/or compared to 1-(4-(4-((2R,4S)-2-(2,4-dichlorophenyl)-2-methyl-1,3-dioxolan-4-yl)methoxy)phenyl)piperazin-1-yl)ethanone. Cytotoxicity can be assayed in an in vitro assay using an epithelial cell line, such as for example those described herein in Experimental Details.

The invention also provides a pharmaceutical composition for antagonizing the human pregnane X receptor (PXR) comprising a compound of the present invention and a pharmaceutically acceptable carrier or diluent. Pharmaceutically acceptable carriers and diluents encompasses any of the standard pharmaceutical carriers or diluents, such as, for example, a sterile isotonic saline, phosphate buffered saline solution, water, and emulsions, such as an oil/water or water/oil emulsions.

The invention further provides a method of preventing or reducing proliferation of tumor cells comprising contacting the tumor cells with an inhibitor of the human pregnane X receptor (PXR). The invention also provides a method of preventing or reducing multidrug resistance in tumor cells comprising contacting the tumor cells with an inhibitor of the human pregnane X receptor (PXR). The inhibitor of the human pregnane X receptor (PXR) can be administered to a subject in an amount and manner effective to inhibit the human pregnane X receptor (PXR) on the tumor cells. The tumor cells can be epithelial or hematologic tumor cells. The tumor cells can be ovarian, colon, cervical or hepatic tumor cells. Preferred inhibitors of the human pregnane X receptor (PXR) include compounds of the present invention.

The effectiveness of different compounds on tumor cells can be assayed using tumor cells grown in in vitro cell culture or in in vivo xenograft models.

The invention also provides a method of inhibiting the human pregnane X receptor (PXR) in a subject comprising administering to the subject a compound of the present invention in an amount and manner effective to inhibit the human pregnane X receptor (PXR). Preferably, administration of the PXR inhibitor increases the transport of a therapeutic drug across the blood-brain barrier and/or increases bioavailability of a therapeutic drug administered through the gastrointestinal tract and/or decreases PXR-mediated cell proliferation and/or decreases PXR-mediated neoplastic transformation.

The compounds of the present invention can be administered to subjects using routes of administration known in the art. The administration can be systemic or localized to a tumor site. Routes of administration include, but are not limited to, intravenous, intramuscular, intrathecal or subcutaneous injection, oral or rectal administration, and injection into a tumor site.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example A

Ketoconazole-Derivative Antagonists of PXR

Materials and Methods

Materials.

Dulbecco's modified eagle medium (DMEM), Lipofectamine™ 2000, heat-inactivated fetal bovine serum (FBS), trypsin-EDTA (0.25%), and penicillin-streptomycin were purchased from GIBCO/Invitrogen (Carlsbad, Calif.). Charcoal/dextran treated fetal bovine serum (FBS) was purchased from Hyclone (Logan, Utah). HepG2 cells were obtained from ATCC (Manassas, Va.). Human PXR-pcDNA3 and luciferase reporter containing CYP3A4 promoter, CYP3A-Luc, were generated at Bristol-Myers Squibb. White TC-surface 384-well plates were purchased from Perkin Elmer (Boston, Mass.). Luciferase substrate (STEADY-GLO®) was purchased from Promega (Madison, Wis.). Alamar-Blue reagent was purchased from Trek Diagnostics (Clevland, Ohio). Rifampicin, ketoconazole and midazolam were purchased from Sigma (St. Louis, Mo.). Human liver microsome and 1-hydroxymidazolam were obtained from BD Biosciences (San Jose, Calif.).

Cell Culture, PXR Transactivation and Cytotoxicity Assays.

HepG2 cells were cultured in DMEM containing 10% FBS. For transient transfection, a transfection mixture containing 1 µg of PXR-pcDNA3 plasmid DNA, 20 µg of Cyp3A-Luc plasmid DNA and 90 µl of Lipofectamine™ 2000 was prepared in 1-ml of serum-free DMEM. The transfection mixture was then applied to the cells in fresh medium (20 ml per flask) and incubated at 37° C. (5% $CO_2$) overnight. The transfected cells were trypsinized and cryopreserved for long-term storage. On the day of experiment, vials of cryopreserved cells were thawed and then resuspended in fresh Media II (DMEM containing 5% charcoal/dextran-treated FBS, 1% penicillin/streptomycin, 100 µM non-essential amino acids, 1 mM sodium pyruvate, and 2 mM L-glutamine). Approximately $8 \times 10^3$ cells were added to wells of 384-well plates containing either test compound alone or a mixture of test compound and rifampicin (10 µM) dissolved in DMSO (0.1% in final incubations). Compounds were tested at ten concentrations (50 µM-2.5 nM, 1:3 serial dilution). The plates then were incubated at 37° C. for 24 hours and subsequently, Alamar Blue reagent was added to each well. Plates were incubated for 2 hours at 37° C., 5% $CO_2$ and then 1 hour at room temperature. Fluorescence was read at Ex525/Em598 to measure cytotoxicity of the test articles. Subsequently, luciferase substrate) (STEADY-GLO®) was added to each well. The plates were incubated for 15 min at room temperature, after which the luminescence was read on a Viewlux (Perkin-Elmer, Waltham, Mass.) plate reader. In addition, drug induced cytotoxicity was assessed by the MTT assay (19, 20) in cancer cell lines (LS174T and SKOV3) as well as a fibroblast cell line (CRL). Cells were exposed to a concentration range of the drug(s) for 48 hours. These assays were repeated three separate times each in triplicate.

Data Analysis.

Rifampicin (10 µM), a well known agonist of PXR, was included in each plate as an internal standard and positive control. The data were then expressed as percent activation (% Act), where the total signal is the signal from the 10 µM rifampicin and the blank signal is that from the DMSO vehicle:

$$\% \, Act = \frac{\text{Compound signal} - \text{Blank signal}}{\text{Total signal} - \text{Blank signal}} \times 100\%$$

For PXR activation, a plot of concentration vs. % Act was generated for each compound tested, and from the plot, concentrations of compound at which 50% activation occurs ($EC_{50}$) and the highest percent activation observed for a particular compound ($E_{max}$) are reported. For PXR inhibition, where the cells were incubated with a mixture of 10 µM rifampicin and the test compound, a percent inhibition (% Inh) was calculated. From the concentration-% Inh plot, concentrations of compound at which 50% inhibition occurs ($IC_{50}$) and the highest percent inhibition observed for that compound ($I_{max}$) are reported.

Statistical Analysis.

Curve-fittings were performed using GraphPad Prism version 5.00 for Windows (GraphPad Software, San Diego, Calif.). Differences in median survival time were determined by the Mann-Whitney U-test. The student t test was used to evaluate the significance of all other data. The high throughput screen in HepG2 cells was repeated once each time in triplicate. Other experiments were repeated three times.

Time-Dependent CYP3A4 Inhibition Assay in Human Liver Microsome.

The CYP3A4 inhibition potential of ketoconazole and its two analogues, FL-B-12 and UCL3158H was tested in human liver microsomes. Briefly, test articles were incubated in a reaction mixture containing 5 µM midazolam, 0.1 mg/ml human liver microsomes and 1 mM NADPH for 5 min. The enzyme reaction was stopped by adding an equal volume of quench solution ($H_2O$:acetonitrileformic-acid=94:5:1) containing $^{13}C$-1-hydroxymdiazolam (0.1 µM final) as the internal standard. In order to test time-dependency of CYP3A4 inhibition, an identical reaction was started without midazolam and the reaction mixture was incubated for 30 min. After the pre-incubation, 5 µM midazolam was added and incubated for 5 min before the quench solution was added. The samples were centrifuged at 1,500 RPM for 15 min to precipitate denatured microsomal proteins. An ultra high-throughput RapdiFire™ mass-spectrometer analysis was performed to measure the quantity of 1-hydroxymidazolam present in the reaction by monitoring mass transition of 342.0→203.1 and 345.0→206.1 for 1-hydroxymidazolam and $^{13}C$-1-hydroxymdiazolam, respectively. A percent CYP3A4 inhibition (% Inh) was calculated by the following equation:

$$\% \, Inh = \left( \frac{C_{DMSO} - C_{compound}}{C_{DMSO}} \right) * 100$$

$C_{DMSO}$ and $C_{compound}$ are concentrations of 1-hydroxymidazolam in the vehicle control and a compound tested, respectively. A plot of concentration-% Inh was then created and from the plot, $IC_{50}$ and Maximum % Inhibition were reported.

Synthesis of Ketoconazole Analogues
Scheme 1:
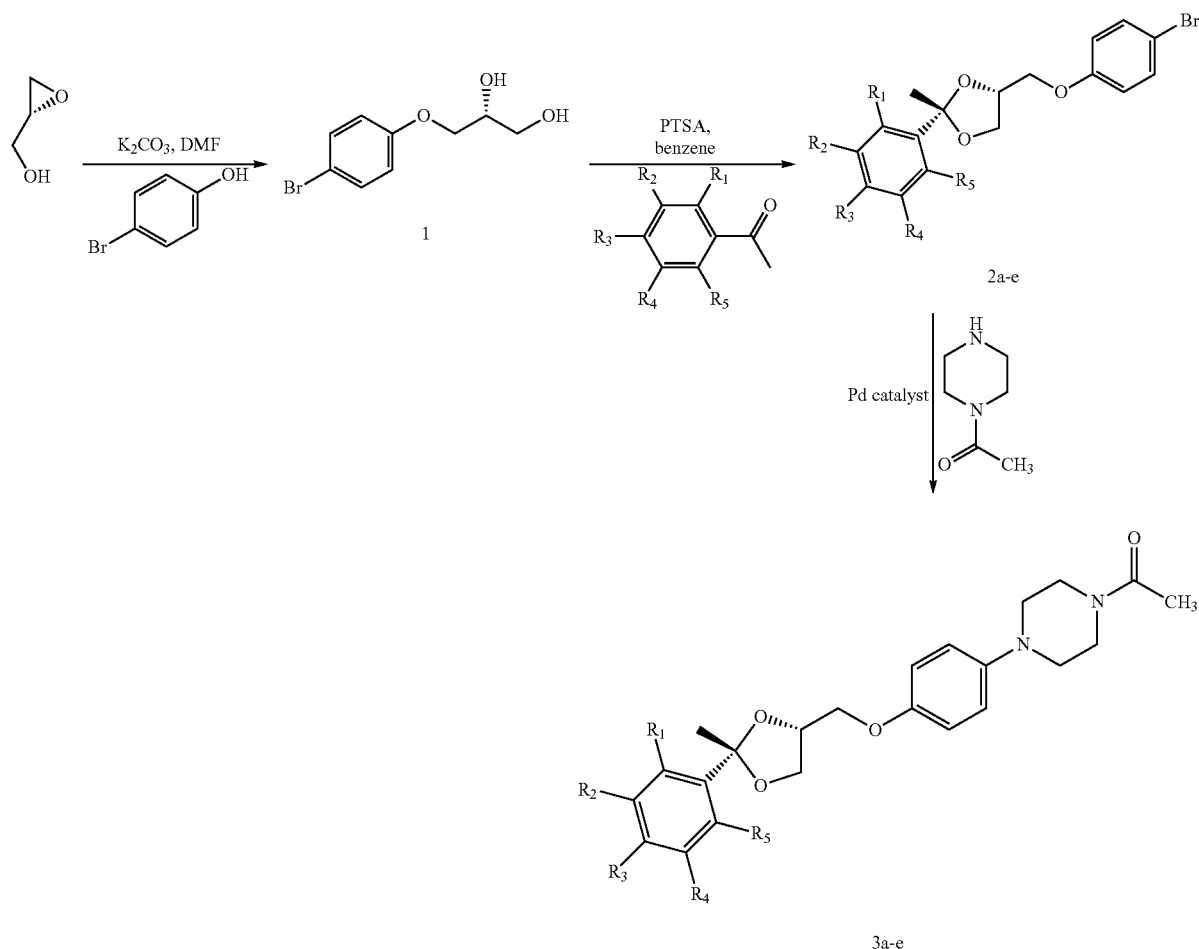
a: $R_1 = H, R_2 = H, R_3 = F, R_4 = H, R_5 = F$
b: $R_1 = H, R_2 = H, R_3 = OCH_3, R_4 = Cl, R_5 = H$
c: $R_1 = H, R_2 = H, R_3 = OCH_3, R_4 = H, R_5 = F$
d: $R_1 = H, R_2 = H, R_3 = OCH_3, R_4 = I, R_5 = H$
e: 2-Decanone
Synthesis of FL-B-12 and Derivatives
Reaction Scheme:
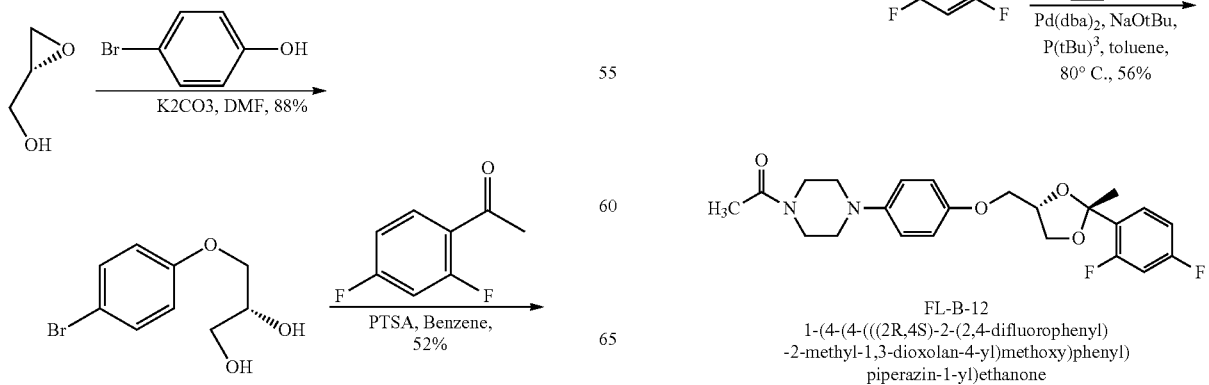
FL-B-12
1-(4-(4-(((2R,4S)-2-(2,4-difluorophenyl)
-2-methyl-1,3-dioxolan-4-yl)methoxy)phenyl)
piperazin-1-yl)ethanone -continued

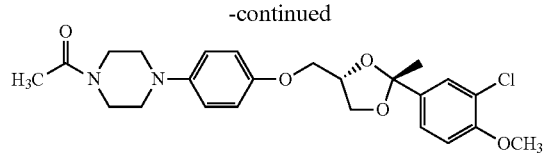

FL-B-15
1-(4-(4-(((2R,4S)-2-(3-chloro-4-methoxyphenyl)
-2-methyl-1,3-dioxolan-4-yl)methoxy)phenyl)
piperazin-1-yl)ethanone

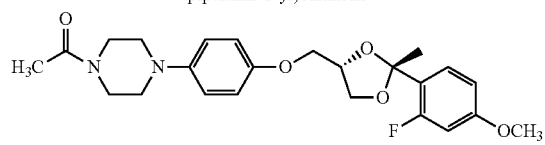

FL-B-24
1-(4-(4-(((2R,4S)-2-(2-fluoro-4-methoxyphenyl)
-2-methyl-1,3-dioxolan-4-yl)methoxy)phenyl)
piperazin-1-yl)ethanone

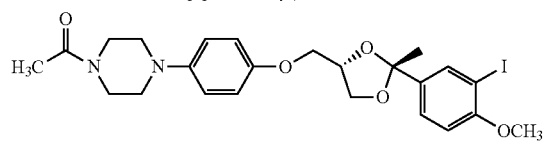

FL-B-31
1-(4-(4-(((2R,4S)-2-(3-iodo-4-methoxyphenyl)
-2-methyl-1,3-dioxolan-4-yl)methoxy)phenyl)
piperazin-1-yl)ethanone

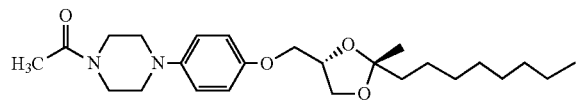

FL-B-45
1-(4-(4-(((2R,4S)-2-methyl-2-octyl-1,3-dioxolan-4-yl)methoxy)
phenyl)piperazin-1-yl)ethanone Synthesis of 1:

$K_2CO_3$ (0.5 equiv, 4.67 g, 33.8 mmol) was added to a stirred solution of (S)-(−)-Glycidol (1 equiv, 5 g, 67.5 mmol) and 4-Bromophenol (3.5 equiv, 41 g, 236.2 mmol) in DMF (150 mL). The reaction mixture was heated at 110° C. overnight. The reaction mixture was, after cooling, added to saturated aqueous $NH_4Cl$ and extracted with ethyl acetate. The organic phase was washed with $H_2O$ and the combined aqueous layers were extracted with ethyl acetate. The organic layers were combined dried with $MgSO_4$ and concentrated. Purification of the residue by silica gel column chromatography (solvent system hexane/ethyl acetate) gave the compound 1. $^1$H-NMR (300 MHz, $CDCl_3$): δ 7.35~7.32 (d, 2H), 6.78~6.75 (d, 2H), 4.06 (m, 1H), 3.96~3.94 (d, 2H), 3.77~3.70 (dd, 2H).

Synthesis of 2a-e:

To a solution of compound 1, R-acetophenone and p-toluenesulfonic acid monohydrate in benzene were heated at reflux for 72 hr, using a Dean-Stark apparatus to remove the separated water. After cooling, the mixture was partitioned between dichlormethane and saturated aqueous sodium hydrogencarbonate and the organic layer was separated. The aqueous layer was extracted with dichloromethane, and the combined organic layer was washed with brine, then dried over magnesium sulfate, filtered, and evaporated. The residue was chromatographied on silica gel to give compound 2a-e:

2a: $^1$H-NMR (300 MHz, $CDCl_3$): δ 7.56~7.51 (m, 1H), 7.38~7.33 (d, 2H), 6.86~6.78 (m, 2H), 6.71~6.66 (d, 2H), 4.62 (m, 1H), 4.33 (m, 1H), 3.98 (m, 1H), 3.83 (m, 2H), 1.76 (s, 3H);

2b: $^1$H-NMR (300 MHz, $CDCl_3$): δ 7.54~7.53 (m, 1H), 7.39~7.35 (m, 3H), 6.93~6.90 (m, 1H), 6.83~6.80 (d, 2H), 4.35 (m, 1H), 4.08 (m, 1H), 3.98 (m, 2H), 3.90 (s, 3H), 3.88 (m, 1H), 1.68 (s, 3H);

2c: $^1$H-NMR (300 MHz, $CDCl_3$): δ 7.90 (m, 1H), 7.37~7.32 (m, 3H), 6.84~6.78 (m, 3H), 4.41 (m, 1H), 4.10 (m, 1H), 3.99 (m, 3H), 3.87 (s, 3H), 1.79 (s, 3H);

2d: $^1$H-NMR (300 MHz, $CDCl_3$): δ 7.93 (m, 1H), 7.47~7.34 (m, 3H), 6.84~6.69 (m, 3H), 4.33 (m, 1H), 4.09 (m, 1H), 3.95 (m, 2H), 3.89 (s, 3H), 3.75 (m, 1H), 1.67 (s, 3H); and 2e: $^1$H-NMR (300 MHz, $CDCl_3$): δ 7.39 (d, 2H), 6.82~6.79 (d, 2H), 4.43 (m, 1H), 4.16 (m, 1H), 4.03 (m, 1H), 3.93~3.87 (m, 2H), 1.40 (s, 3H), 1.32~1.22 (m, 17H).

Synthesis of 3a-e:

A mixture of compound 2a-e, 1-Acetylpiperazine, t-BuONa, P(tBu)$_3$ and Pd(dba)$_2$ in dry toluent was gently refluxed with stirred under a nitrogen atmosphere for 18 h. The mixture was added 10 mL water, extracted with ethyl acetate (20 mL×3), washed with water (10 mL), and brine (15 mL). The extracts were dried over $Na_2SO_4$ and evaporated off. The residue was purified by column chromatography on silica gel to give 3a-e:

3a: $^1$H-NMR (300 MHz, $CDCl_3$): δ 7.52 (m, 1H), 6.87~6.71 (m, 6H), 4.58 (m, 1H), 4.28 (m, 1H), 3.95 (m, 1H), 3.76 (m, 4H), 3.58 (m, 2H), 3.00 (m, 4H), 2.11 (s, 3H), 1.72 (s, 3H);

3b: $^1$H-NMR (300 MHz, $CDCl_3$): δ 7.50 (m, 1H), 7.33 (m, 1H), 6.88~6.74 (m, 5H), 4.52 (m, 1H), 4.28 (m, 1H), 4.06 (m, 1H), 3.99 (m, 2H), 3.84 (s, 3H), 3.71 (m, 2H), 3.56 (m, 2H), 3.02 (m, 4H), 2.09 (s, 3H), 1.62 (s, 3H);

3c: $^1$H-NMR (300 MHz, $CDCl_3$): δ 7.38 (m, 1H), 6.85 (m, 3H), 6.73 (d, 1H), 6.59 (m, 2H), 4.55 (m, 1H), 4.35 (m, 1H), 4.06 (m, 1H), 3.90 (m, 2H), 3.75 (s, 3H), 3.71 (m, 2H), 3.56 (m, 2H), 3.00 (m, 4H), 2.10 (s, 3H), 1.74 (s, 3H);

3d: $^1$H-NMR (300 MHz, $CDCl_3$): δ 7.42 (d, 1H), 7.17 (dd, 1H), 7.05 (m, 1H), 6.88 (m, 4H), 4.62 (m, 1H), 4.31 (m, 1H), 4.08 (m, 1H), 3.93 (m, 2H), 3.87 (s, 3H), 3.76 (m, 2H), 3.62 (m, 2H), 3.04 (m, 4H), 2.13 (s, 3H), 1.66 (s, 3H); and 3e: $^1$H-NMR (300 MHz, $CDCl_3$): δ 6.82 (m, 4H), 4.37 (m, 1H), 4.11 (m, 1H), 3.98 (m, 1H), 3.84 (m, 2H), 3.72 (t, 2H), 3.56 (t, 2H), 3.00 (m, 4H), 2.09 (s, 3H), 1.38 (m, 21H).

Results

The basis for structure-function analysis of inhibitors of activated PXR comes from the initial observations that ketoconazole is a weak activator of PXR but an inhibitor of activated PXR ($IC_{50}$=18.73 µM) (Table 1). Based on previous modeling studies, a site of inhibition may include the AF-2 surface (11, 14-15, 17-18). Ketoconazole induces toxicity at high doses in humans. This may be partly due its inhibitory activity against heme-iron containing enzymes, which is attributed to the imidazole group (21, 22). Analogs of ketoconazole were designed that lacked the imidazole group to see if this modification impinged on PXR activity. These compounds developed at University College London (UCL), were tested in the PXR transactivation assay. Among 7 UCL compounds tested, UCL2112H (21) did not transactivate PXR nor inhibit the rifampicin-mediated activation of the receptor, whereas UCL2238 (24) was a potent activator of PXR but was not an inhibitor. However, other compounds behaved like ketoconazole, being a weak activator of PXR and a moderate antagonist of activated PXR. UCL2158H (21) and UCL2202D (21) appeared to be the most potent inhibitors of PXR. UCL2158H appeared to be a better PXR antagonist than UCL2202D since UCL2202D moderately activated PXR (43%) while UCL2158H did not elicit a significant PXR activation (10%). The FL compounds in Table 1 are fluorinated derivatives of ketoconazole lacking the imidazole group, synthesized at Albert Einstein College of Medicine. Five FL compounds were tested and all showed a varying degree of PXR antagonism. However, except for FL-B-12, all showed a moderate potent activation of PXR in addition to their activities against rifampicin-mediated PXR activation. FL-B-12 did not significantly activate PXR (10%) but inhibit PXR activation by rifampicin to a full extent (103%). These results indicate that the removal of the imidazole group from ketoconazole or its analogues did not significantly alter their ability to inhibit PXR.

Subsequently, the effects of the loss of the imidazole group were examined on CYP inhibition associated with the parent compound, ketoconazole, in human liver microsomes using midazolam as the CYP3A4-specific substrate. In addition, a time-dependency of a potential CYP inhibition was tested to see if the loss of imidazole group brings about new liabilities previously not associated with ketoconzole by preincubating the compounds with microsome. Two compounds, UCL2158H and FL-B-12, were chosen for this study along with ketoconazole as the positive control. Table 3 illustrates the $IC_{50}$ values with and without preincubation with the test compounds. Ketoconazole, a prototypical reversible inhibitor of CYP3A4 (and thus midazolam 1-hydroxylase activity), completely inhibits conversion of midazolam to its metabolite (103% inhbition with an $IC_{50}$ of 0.020 µM) with no indication of time dependency (no $IC_{50}$ change). In the same assay performed simultaneously using the same pool of microsomes, UCL2158H was shown to be a weak inhibitor ($IC_{50}$ of 10.8 or 19.6 µM) of CYP3A4 which demonstrated no time-dependency. FL-B-12 appears to be a very weak activator of CYP3A4 ($IC_{50}$>40M), again without a time-dependency of its CYP3A4 inhibition. Hence the elimination of midazolam group in these analogues markedly improved CYP3A4 inhibition compared to ketoconazole without introducing new liability (time-dependent inhibition).

In a cytotoxicity screen that was performed simultaneously with PXR transactivation assay, some of the tested compounds including ketoconazole were toxic in HepG2 cells with 24 hours incubation especially at the highest concentration tested (50 µM) (data not shown). Thus, the cytotoxic potential for the most potent PXR antagonists (FL-B-12 and UCL-2158H) were tested in three cancer cell lines (Caco-2, LS174T and SKOV3) as well as in a transformed fibroblast cell line (CRL). These compounds (UCL2158H and FL-B-12) were less cytotoxic than ketoconazole in these epithelial cells across a concentration range up to 100 µM (FIG. 3). FL-B-12 was the least cytotoxic (~98% viability across all cell lines tested) in the effective concentration range for PXR inhibition (e.g., two times the $IC_{50}$~30 µM). However, in the same concentration range, ketoconazole is cytotoxic (viability is ~65-75% across all cell lines tested). These results together showed that FL-B-12 and UCL2158H have better cytotoxic profiles than ketoconazole, that FL-B-12 has a better profile than UCL2158H and that the PXR inhibition exhibited by these compounds was not a result of cell death induction.

TABLE 1

Maximum activation and inhibition of PXR transactivation by ketoconazole and its derivatives.

| Substance (Ref) | Maximum % Activation Observed | Maximum % Inhibition Observed |
|---|---|---|
| Ketoconazole | 20 | 93 |
| UCL2112H (21) | 0 | 0 |
| UCL2134D (23) | 2 | 82 |
| UCL2135 (23) | 10 | 32 |

TABLE 1-continued

Maximum activation and inhibition of PXR transactivation by ketoconazole and its derivatives.

| Substance (Ref) | Maximum % Activation Observed | Maximum % Inhibition Observed |
|---|---|---|
| UCL2158H (21) | 10 | 109 |
| UCL2202D (21) | 43 | 108 |
| UCL2245 (24) | 2 | 58 |
| UCL2238 (24) | 91 | 1 |
| FL-B-12 | 10 | 103 |
| FL-B-15 | 36 | 90 |
| FL-B-24 | 50 | 75 |
| FL-B-31 | 33 | 59 |
| FL-B-45 | 72 | 48 |
| Rifampicin | 107 | 18 |

$EC_{50}$, concentration required for activation of PXR to 50% of maximum as seen with 10 µM rifampicin;
$E_{max}$, maximal activation observed compared to that seen with 10 µM rifampicin;
$IC_{50}$, concentration required to antagonize 10 µM rifampicin mediated PXR activation by 50%;
$I_{max}$, maximal inhibition of PXR activation with 10 µM.

TABLE 2

Non-linear regression analysis of PXR activation and PXR inhibition by rifampicin and ketoconazole, FL-B-12 and UCL2158H.

| | PXR Activation | | PXR Inhibition | |
|---|---|---|---|---|
| Substance | $EC_{50}$ | $E_{max}$ | $IC_{50}$ | $I_{max}$ |
| Ketoconazole | >50 µM | — | 18.73 µM | 93% |
| UCL2158H | >50 µM | — | 14.61 µM | 128% |
| FL-B-12 | >50 µM | — | 13.68 µM | 104% |
| Rifampicin | 0.78 µM | 94% | >50 µM | — |

$IC_{50}$: Concentration required to inhibit 50% of effect (activation by rifampicin);
$I_{max}$: maximal inhibition of PXR activation with 10 µM rifampicin.

TABLE 3

Inhibition of midazolam-1-hyxroxylase activity by ketoconazole, FL-B-12 and UCL2158H in human liver microsome with and without preincubation with the test articles.

| | −preincubation | | +preincubation | |
|---|---|---|---|---|
| Substance | $IC_{50}$ | Maximum % Inhibition | $IC_{50}$ | Maximum % Inhibition |
| Ketoconazole | 0.020 µM | 103% | 0.026 µM | 102% |
| FL-B-12 | >40 µM | 20% | >40 µM | 37% |
| UCL2158H | 10.8 µM | 80% | 19.6 µM | 67% |

Example B

Role of PXR in Cancer

Materials and Methods

Plasmids and Reagents.

CREMOPHOR®EL and rifampicin were obtained from Sigma Chemical Co. (St. Louis, Mo.). Hyperforin was purchased from Cayman Chemical Co. (Ann Arbor, Mich.). GlaxoSmithKline (Dr. J. Collins, Research Triangle, Durham, N.C.) and SN-38 by Enzon Pharmaceuticals (Dr. O, Sachdev, Piscataway, N.J.) supplied T0901317 (T1317) and GSK1385, respectively. Bristol-Myers Squibb (Dr. F. Lee, Princeton, N.J.) supplied BMS-247550 (ixabepilone). Clinical grade paclitaxel was obtained from the Albert Einstein College of Medicine (AECOM) Pharmacy (Bronx, N.Y.). Paclitaxel was formulated in CREMOPHOR® EL and hyperforin in methanol. All the other compounds were dissolved in 100% dimethyl sulfoxide (DMSO) and stored at −20° C. The final concentration of DMSO was ≤0.2% in all experiments. The polyclonal PXR antibody used for Western blot analysis was a kind gift from Dr. R. K Tyagi (Jawaharlal University, New Delhi, India). The polyclonal PXR antibody used for immunohistochemistry was purchased from BioLegend, Inc (San Diego, Calif.).

Cell Culture.

HepG2 (ATCC, Mansassas, Va.) and OVCAR-8 cells (kind gift from I. David Goldman, Bronx, N.Y.) were maintained in RPMI 1640 supplemented with 10% FBS. SKOV-3 cells were a gift from Dr. Gloria Huang (Bronx, N.Y.) and were maintained in MEM alpha supplemented with 13% FBS. When indicated, cells were propagated in charcoal-adsorbed sera and phenol-free media.

Immunoblotting.

The presence of PXR in SKOV-3 and HepG2 nuclear protein fraction was determined by Western blot analysis. Protein concentration was determined via the modified Bradford assay using the NanoDrop ND-100 Spectrophotometer (Wilmington, Del.). Nuclear fraction was isolated using the BioSource Nuclear Extraction Kit (Invitrogen, Carlsbad, Calif.) per manufacturer's instructions. 40-200 µg of nuclear protein was resolved by 12% SDS-PAGE and transferred to nitrocellulose. The blot was probed with a 1:10,000 dilution of a polyclonal PXR antibody as described previously (25) and developed using the LI-COR Odyssey Infrared Imager (Lincoln, Nebr.). The Western blot analysis was performed in duplicate.

Immunochemistry.

HepG2 cells were processed into slides using histogel (Richard-Allan Scientific, Kalamazoo, Mich.). The slides were placed in a 59° C. oven in the morning of the experiments. For cells and tissue specimens, after de-waxing and re-hydrating the slides, slides were placed in a sodium citrate solution, pH 6.0 (Vector labs, Burlingame, Calif.) for 20 minutes. The cells were then sequentially blocked with a 3% peroxidase blocking solution and 2% BSA and 5% donkey serum in TBS for 1-2 hours. Cells were incubated with 1:40 dilution of the primary polyclonal PXR antibody (Biolegend, Inc) or Ki67 antibody (clone Ki-S5; #ab28025, Abcam, Cambridge, Mass.) for 12 hours or at 4° C. overnight followed by the biotinylated secondary antibody for 1 hour. Cell sections were then immunostained with the biotin-streptavidin system from Vector Labs per manufacturer's instructions. Institutional IRB approval (#2007-902) was obtained for use of tissue sections from patients with serous papillary ovarian carcinoma and benign ovaries.

Semi-Quantitative RT-PCR and Real-Time RT-PCR.

Experiments were carried out as described previously (11). In brief, total RNA was isolated using the Qiagen RNeasy Mini kit (QIAGEN, Inc., Valencia, Calif.). Reverse transcription was performed using Superscript first strand synthesis system (Invitrogen, Carlsbad, Calif.). For semi-quantitative PCR, one-tenth the reverse transcription (RT) reaction products were subjected to PCR amplification for 25 cycles in a singleplex format. The forward primer for PXR was 5'-GAGCTGATGGACGCTCAG-3' (SEQ ID NO:1) and reverse 5'-TGGCAAAGCTGATGATGC-3' (SEQ ID NO:2). GAPDH was used as an internal control with the following forward and reverse primers: 5'-TGCATCCTGCACCAC-CAAC-3' (SEQ ID NO:3) and 5'-CGCCTGCTTCACCAC-CTTC-3' (SEQ ID NO:4), respectively. Real time PCR for cDNA quantification was performed using TaqMan universal PCR master mix and TaqMan probes using, VIC as the 5' reporter fluorochrome and tetramethylrhodamine (TAMRA) as the 3' quencher fluorochrome. Simultaneous quantification of the 18S RNA using a kit from ABI systems (Cat #: 4308329) allowed for normalization between samples. The reference gene, PPIA (Cyclophilin A), was a VIC/MGB probe (Applied Biosystems, Foster City, Calif.). The standard curves for PXR, CYP3A4, CYP2B6, UGT1A1, MDR1, and MRP-2 cDNA were constructed to ensure linearity in the concentration range studied. The PXR assay (ID #Hs01114267_m1) and the UGT1A1 assay (ID # Hs02511055_s1) were ordered through Applied Biosystems. The CYP3A4 forward primer sequence was 5'-TGGTGAAT-GAAACGCTCAGATT-3' (SEQ ID NO:5), the CYP3A4 reverse primer sequence was 5'-CATCTTTTTTGCAGAC-CCTCTCA-3' (SEQ ID NO:6), and the CYP3A4 probe sequence was 5'-VIC-TTCCCAATTGCTATGAGAC (SEQ ID NO:7)-TAMRA-3', all spanning exon junctions, thus preventing amplification of genomic DNA. The CYP2B6 forward primer sequence was 5'-GACCGAGCCAAAATGC-CATA-3' (SEQ ID NO:8), the reverse primer sequence was 5'-GGTCGGAAAATCTCTGAATCTCA-3' (SEQ ID NO:9), and the probe sequence was 5'-VIC-ACAGAGGCAGT-CATC (SEQ ID NO:10)-TAMRA-3'. The MDR-1 Forward primer sequence was 5'GGAAGCCAATGCCTAT-GACTTTA-3' (SEQ ID NO:11), the reverse primer sequence was 5'-ACTCAACTGGGCCCCTCTCT-3' (SEQ ID NO:12), and the probe sequence was 5'-VIC-CATGAAACTGCCT-CATAAATTTGACACCCTG (SEQ ID NO:13)-TAMRA-3'. The MRP-2 forward primer sequence was 5'-GGCTGT-TGAGCGAATAACTGAGT-3' (SEQ ID NO:14), the reverse primer sequence was 5'-GCCTTTGCTGGGCCAAT-3' (SEQ ID NO:15), and the probe sequence was 5'-VIC-AAAAT-GAGGCACCCTGGGTGACTGATAAGA (SEQ ID NO:16)-TAMRA-3'. Amplification was detected and analyzed using the ABI PRISM 7700 sequence detector with SDS 2.1 analysis software (Applied Biosystems, Foster City, Calif.). The relative fold increase in mRNA in samples compared with controls was calculated using the comparative CT method.

Cell Survival (MTT) Assay.

Aliquots of $2 \times 10^3$ SKOV-3 cells were plated in 96-well plates in at least triplicates. Cells were treated with serial dilutions of each drug. Following incubation for 24-120 hours, the MTT assay was performed as previously described (19). Media with drug was changed every 72 hours. The vehicle was 0.2% DMSO.

Chemotherapeutic Sensitivity Assay.

SKOV-3 cells were incubated in complete media with and without 20 µM rifampicin for 48 hours. At 48 hours, cells were trypsinized, and aliquots of $5 \times 10^3$ cells were plated in 96-well plates in triplicates with or without 20 µM of rifampicin. After 24 hours of incubation at 37° C., cells were treated with serial dilutions of the chemotherapeutic agent. After a further 48 hours of incubation, the MTT assay was performed as described previously (19).

In Vivo SKOV-3 Xenograft Studies.

$2 \times 10^6$ SKOV-3 cells were implanted by subcutaneous route into both flanks of NOD.SCID mice. On day 35 after inoculation, the mean (±SD) (n=32) volume of implanted tumor was 8 mm³ (±3.5) (range: 4.3-18.3). Sixteen mice were selected from this pool (mean tumor volume [±SD] 6.1 [±3.4]) for rifampicin injections and another sixteen (mean tumor volume [±SD] 10.1 [±4.8]) for control injections. Rifampicin was formulated in 30% polyethylene glycol and dosed by direct venous (tail vein) injection at 40 mg/kg/day over three consecutive days repeated every 7 days. Control intravenous injections consisted of 30% polyethylene glycol.

The tumor volume was calculated twice a week using the following formula: Length (mm)×[Width (mm)]$^2$×π/6 (25).

Statistical Analysis.

The significance of numerical comparisons (values) between groups were made using the student t-test (either unpaired or paired, two-tailed, equal variance or unequal variance) (MICROSOFT® Excel X forMAC®). Descriptive statistics were used to calculate mean, standard deviation and standard error of mean. For FIG. 7, SigmaPlot 9.0 (Systat Software, Inc, Point Richmond, Calif.) was used to generate a simulation curve to data analyzed using regression wizard (Emax model).

Results

Expression of PXR in SKOV-3 Cell Line and Ovarian Tissue.

PXR is expressed in two ovarian cancer cell lines, SKOV-3 and OVCAR-8. MB-468 and SKOV3 cells express PXR mRNA. In quantitative RT-PCR studies, SKOV-3 cells express PXR mRNA approximately 3.8-fold over that observed in OVCAR-8 cells. PXR is expressed at the protein level in both SKOV-3 and OVCAR-8 cells; however, no such expression is observed for MB-468 (MDA-MB-468) cells. The latter cell line has been shown to have very low or undetectable levels of PXR mRNA (26). PXR is clearly detected by immunochemistry as speckled bodies within the nucleus of human ovarian carcinoma tissue.

PXR Activation Induces PXR Target Genes in SKOV-3 Cells.

Quantitative RT-PCR was performed to determine which of known target genes of PXR were amplified in the ovarian cancer cell line. When SKOV-3 cells were treated with 20 μM of rifampicin, an approximately >10-fold increase was detected in CYP3A4, CYP2B6, and nearly 8.5-fold increase in UGT1A1 mRNA. Importantly, there was no increased transcription of MDR-1 or MRP-2 genes. The same experiments were repeated using a 0-1.0 μM concentration range for T0901317 (potent PXR agonist; $EC_{50}$=80-125 nM) and its inactive analog, GSK1385 ($EC_{50}$>>1000 nM) (27, 28) (data on GSK1385 is unpublished and provided by Dr. M. Redinbo, UNC Chapel Hill, N.C.). The same profile of gene expression was observed with T1317 and with rifampicin. There was no PXR target gene induction with GSK1385. Together these data clearly indicate that PXR in SKOV-3 cells is functional and has tissue-specific gene targets.

PXR Activation Induces SKOV-3 Cell Proliferation In Vitro.

Figure 4A:
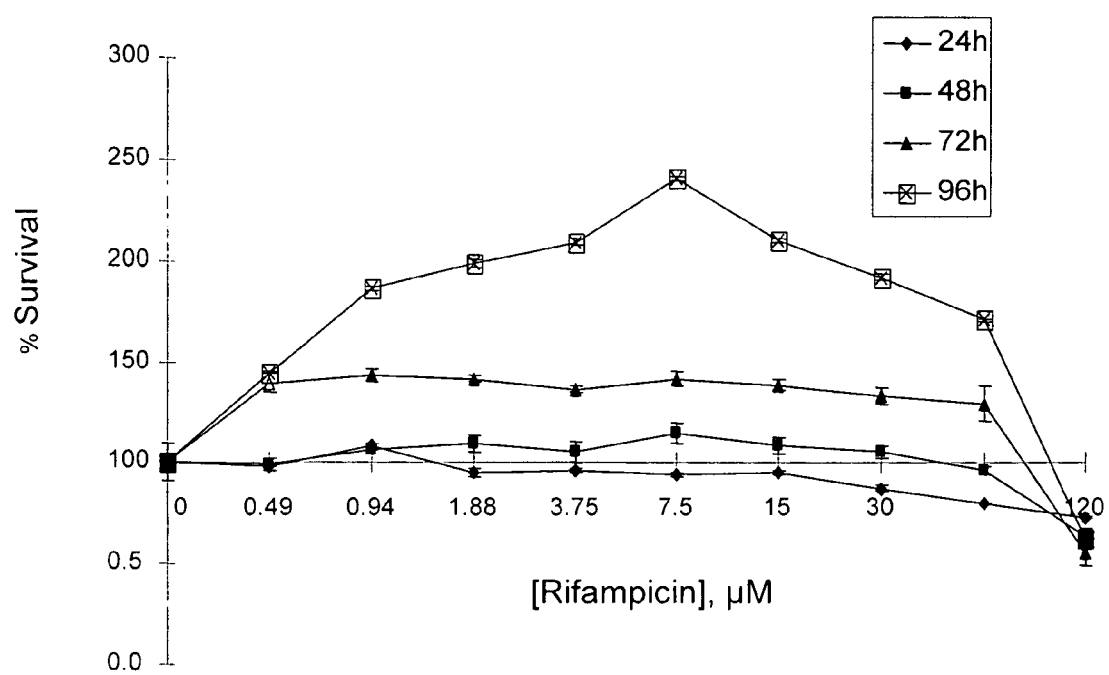
FIG. 4A-4C. SKOV-3 cell proliferation in the presence of PXR ligands. SKOV-3 cells were treated with (A) rifampicin (0.49-120 μM) or (B) hyperforin (0.05-1 μM) or (C) T0901317 (T1317) or GSK1385 (both ranging between 0.05-1 μM) over a duration ranging between 24-96 h. For experiments illustrated in (C), only data from the 48 h time-point of drug(s) exposure are shown. Similar data has been shown for 72 hours (data not shown). The Y-axis represents a Fractional Survival value defined by the Fold survival (S) observed with compound T1317 (denoted, $S_{T1317}$) divided by the Fold Survival observed with compound GSK1385 (denoted, $S_{GSK}$). The X-axis shows the concentrations for both drugs (e.g., 0.05 means 0.05 μM for T1317 and for GSK). To interpret the graph, the fractional survival when no drug(s) are present {$S_{T1317}/S_{GSK}$} by definition is 1. Any positive value thereafter implies a growth advantage for T1317 over GSK. At the end of each time point of drug exposure, cells were subject to MTT assay (see Materials and Methods). The % survival was calculated from $OD_{490}$ ratios of treated divided by control (vehicle treated) wells (minus the blank)×100 (expressed and plotted as a percentage growth over control cells). Experiments were repeated four separate times each in triplicate. Individual points represent mean (±SD).
Figure 4B:
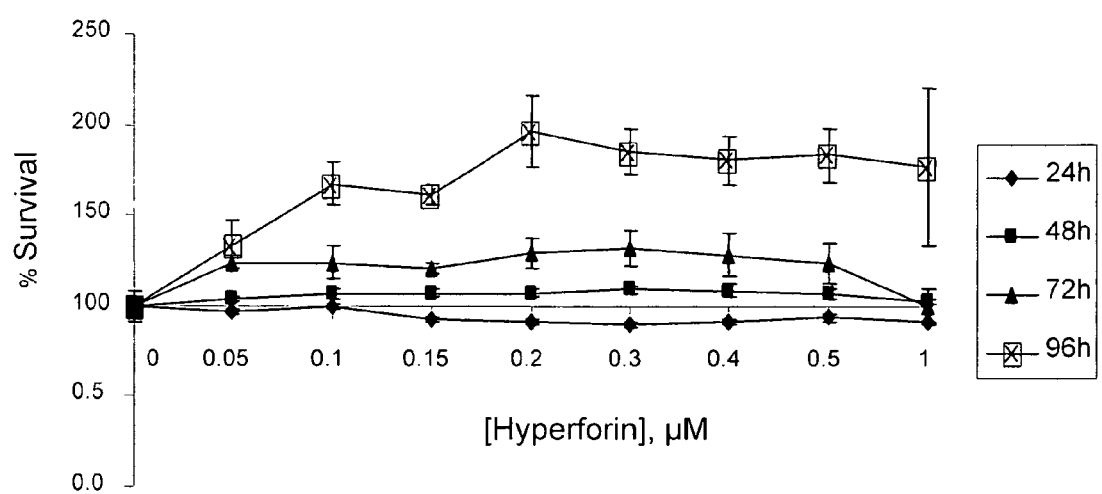
Figure 4C:
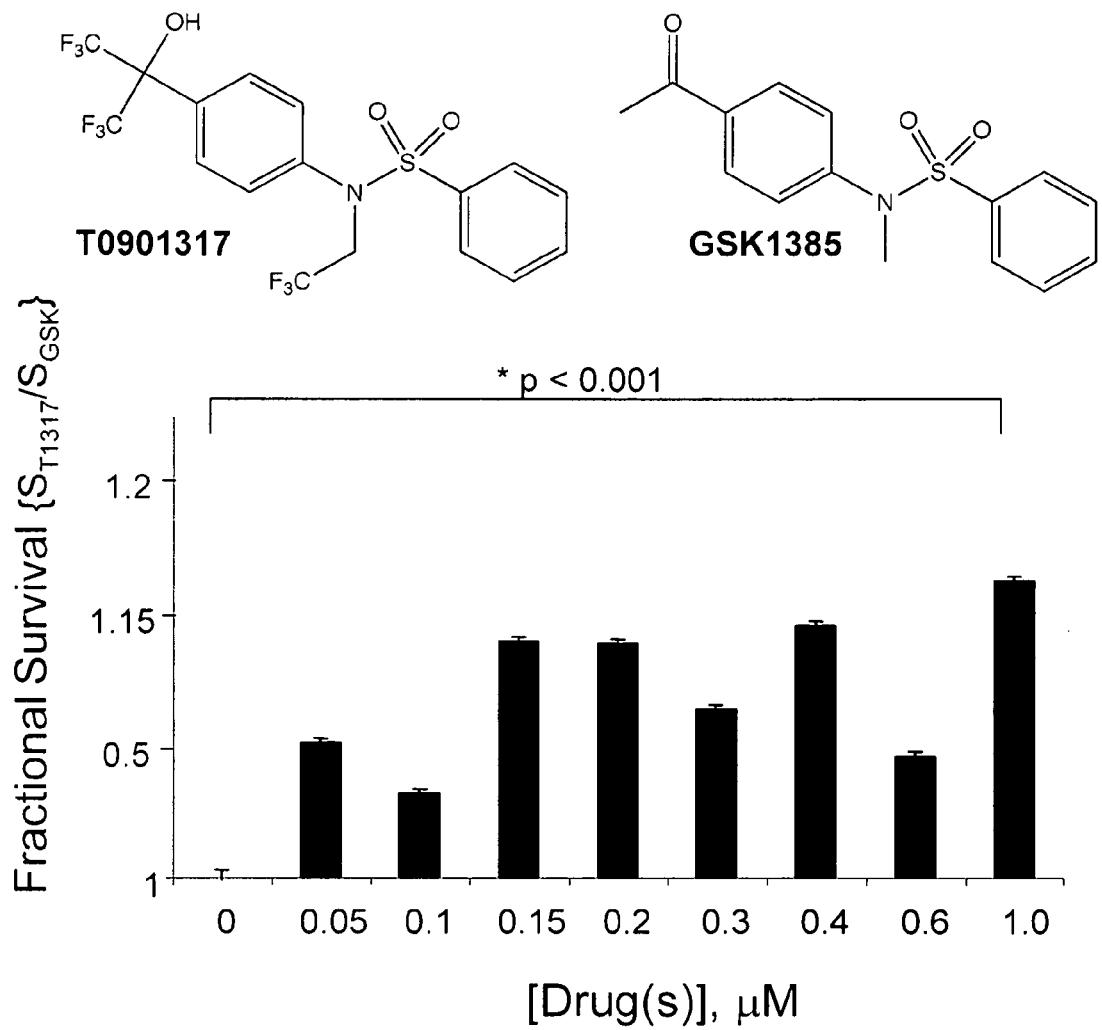

The role of PXR in cancer cell growth has previously been unclear. SKOV-3 cells were treated with ligands known to activate PXR: rifampicin ($EC_{50}$=1-2 μM), hyperforin ($EC_{50}$=23 nM), and T1317 (PXR $EC_{50}$=80-125 nM; LXR $EC_{50}$>190 nM). The latter is an investigational anti-cholesterol drug that is a dual PXR/LXR agonist (27, 28); however, at a concentration range between 0-1.0 μM serves as a more potent PXR agonist. Rifampicin (0.49-60 μM), a known PXR agonist, induces a significant increase in cell survival and the longer the duration of exposure to rifampicin, the greater is the effect on cell survival (compare 48, 72 and 96 hr exposures, FIG. 4A) (29). Similar data using rifampicin has been shown for OVCAR-8 cells. Hyperforin (0.05-1 μM), a known potent PXR agonist, also induces a significant increase in cell survival and the longer the duration of exposure to hyperforin, the greater is the effect on cell survival (compare 48, 72 and 96 hr exposures, FIG. 4B) (30). To further confirm the effect of PXR activation on cell survival, SKOV-3 cells were treated with T1317 or GSK1385 (0-1.0 μM) for 48 hours and then MTT assay was performed to determine cell survival fraction. The data were then expressed as fold survival when treated with the PXR agonist, T1317 normalized to survival at the same concentration of GSK1385. There is a significant increase in cell survival with T1317 over the concentration range 0.05-1.0 μM, suggesting that PXR activation directly contributes to cell survival (FIG. 4C).

Figure 5:
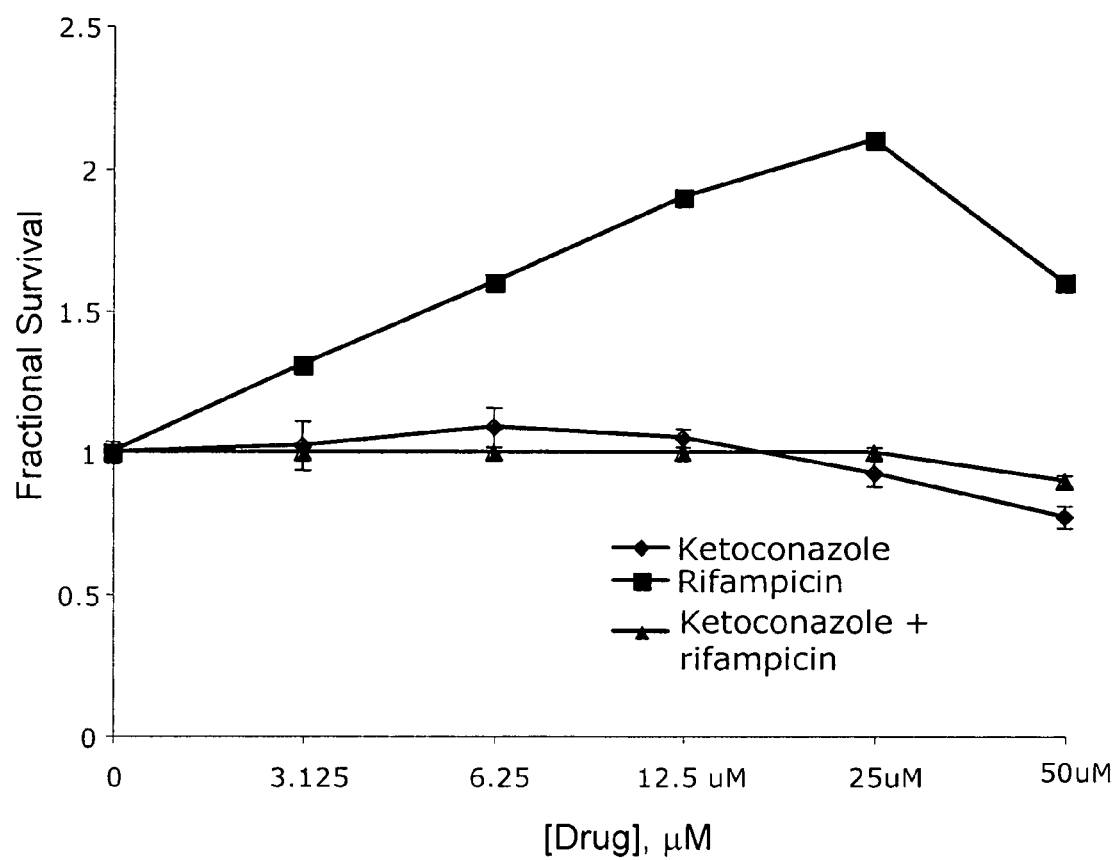
FIG. 5. HepG2 cell proliferation in the presence of Rifampicin and/or Ketoconazole. HepG2 cells were treated with rifampicin (0-50 μM) or ketoconazole (0-50 μM) or both drugs each at the same concentration over a 48 hour duration. At the end of each time point of drug exposure, cells were subject to MTT assay (see Materials and Methods). The fractional survival was calculated from $OD_{490}$ ratios of treated divided by control (vehicle treated) wells (minus the blank). Experiments were repeated four separate times each in triplicate. Individual points represent mean (±SD).

HepG2 cells were treated with rifampicin, ketoconazole or a concentration range of ketoconazole in the presence of rifampicin for 48 hours. The MTT survival assay was performed to determine viability of cells. In HepG2 cells, rifampicin induces a concentration dependent proliferation of cells. Ketoconazole has minimal effects until a concentration of 12.5 μM, when ~15% of cells are non-viable and by 50 μM, >35% of cells are non-viable. However, when a combination of ketoconazole and rifampicin is tested, cell proliferation is clearly decreased (FIG. 5). While these data cannot completely exclude off-target effects of ketoconazole, it is likely that inhibition of rifampicin-activated PXR by ketoconazole contributes towards decreased cell proliferation. In comparing all the data, specifically, the ability of different PXR agonists to enhance cell proliferation of SKOV-3 cells, it appears that the relative known potency of each agent mirrors its potency in enhancing cell proliferation.

PXR Activation Induces SKOV-3 Cell Proliferation In Vivo.

Figures 6A, 6B, 6C:
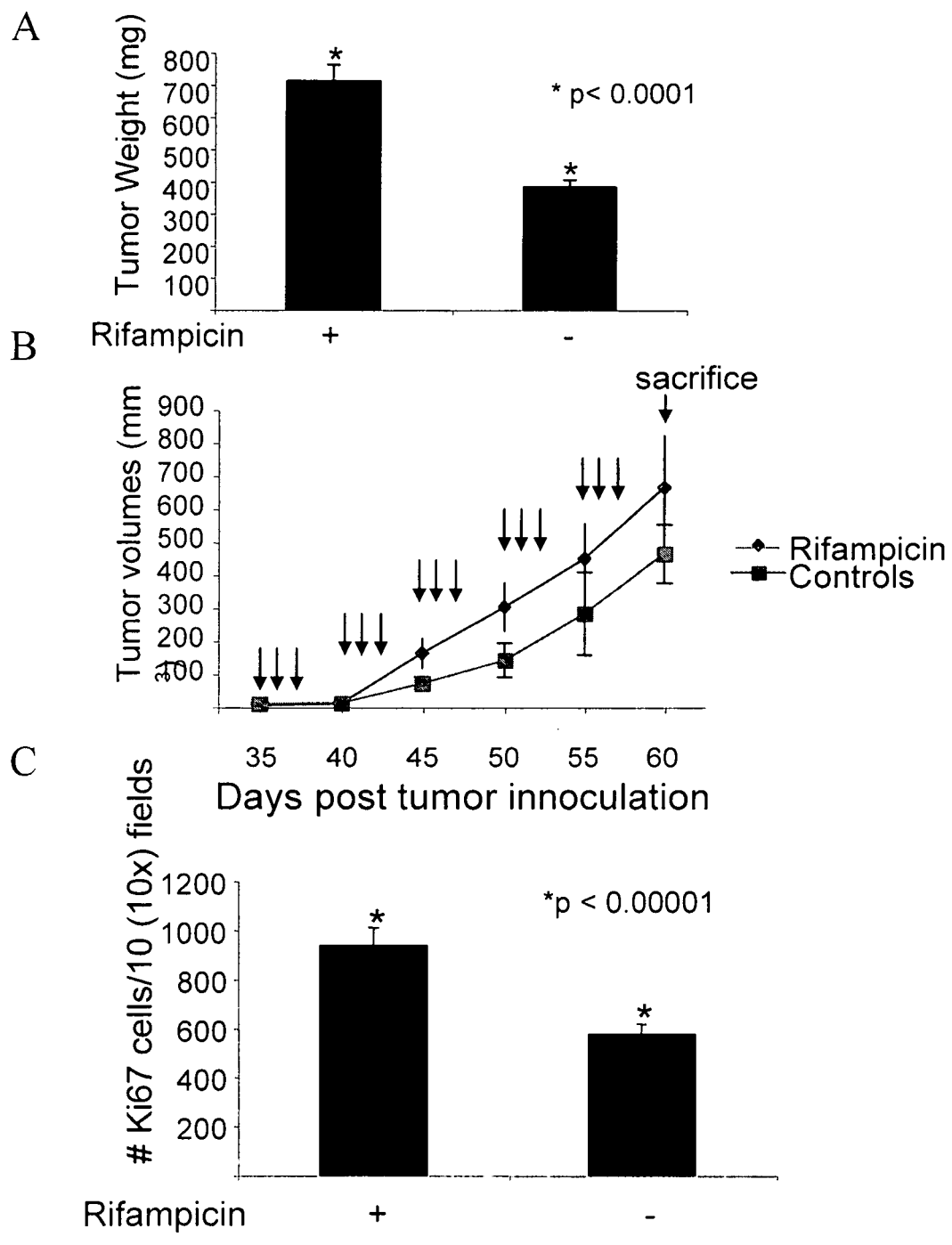
FIG. 6A-6C. SKOV-3 mouse xenografts treated with rifampicin or vehicle. Sixteen NOD.SCID mice carrying SKOV-3 xenografts in both flanks were treated with rifampicin three times per week (as indicated by arrows in B) continuously from days 35-60. Tumor volumes were assessed as described in Materials and Methods. (A) Tumor weights (mg) as assessed on day 60 for rifampicin-treated (n=32 tumors) and control group (n=32 tumors). Bar, mean (±SEM); (B) Tumor volumes (n=32) measured on day 5 after the first injection of each week. Points represent mean (±SEM); (C) Ki67 staining of SKOV-3 xenografts. Multiple (8-10) sections per tumor (n=3 tumors per treatment group) were assessed. Quantitation of Ki67 positive cells (n=32) was performed under 10× magnification visually by counting cells randomly over 10 high power fields (10×). Bar, mean (±SD).

To validate the in vitro effects of PXR activation on SKOV-3 cancer cell growth, NOD.SCID mice carrying SKOV-3 xenografts were treated with or without rifampicin. Rifampicin treated mice consistently had significantly larger tumors on both visual inspection at necropsy (day 60) as well as by tumor weight (FIG. 6A). The tumor volumes were assessed twice weekly and these values were significantly higher for the rifampicin treated group as compared with controls (days 45-60) (FIG. 6B). Assessment for proliferation in tumor cells was performed using Ki67 antibody. The immunohistochemistry show that there is a significant increase in cell proliferation (increased Ki67 stained cells) in tumors from mean (SEM) rifampicin treated versus control mice [937.0 (37) vs 577.0 (21), p<0.00001; FIG. 6C]. These data validate the in vitro findings that PXR activation induces cell growth (proliferation) and survival.

PXR Activation Induces Multi-Drug Resistance in SKOV-3 Cells.

Figure 7A:
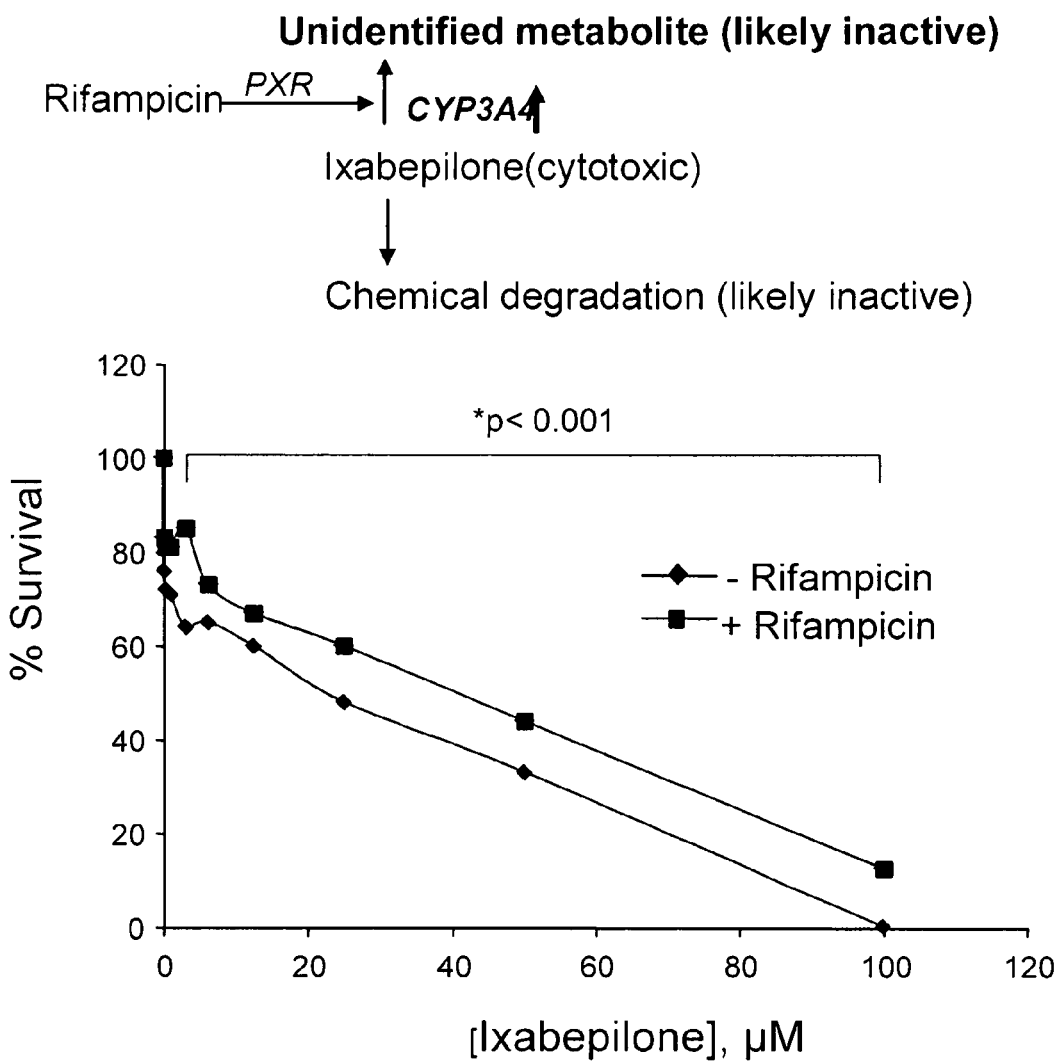
FIG. 7A-7C. Cell cytotoxicity from anti-cancer xenobiotics in SKOV-3 cells pretreated with rifampicin or vehicle. SKOV-3 cells were pretreated (for 24 hours) with 15 μM rifampicin or vehicle and then exposed to (A) ixabepilone (0.1-100 μM) or (B) paclitaxel (0.05-50 μM) or (C) SN-38 (0.05-20 μM) for another 24 hours. Then inset figures B(i) and B(ii) show the effects of 3α-OH and 6α-OH paclitaxel treatment of SKOV-3 cells for 24 hours, respectively. Each experiment was performed three times in triplicate. Individual points and Bar, mean (±SD). The statistical significance is shown as a *p-value on the figure across the annotated concentration range.
Figure 7B:
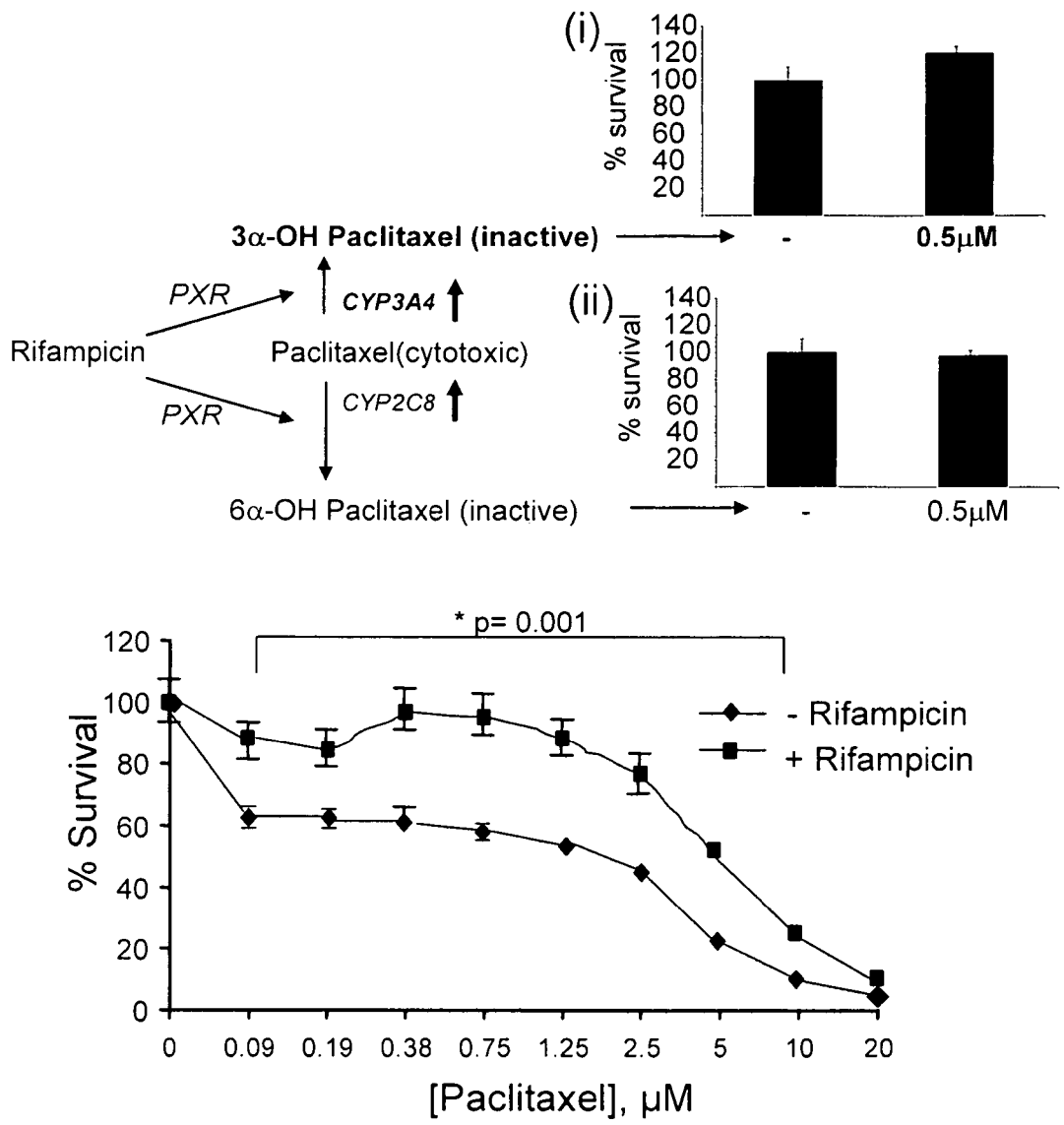
Figure 7C:
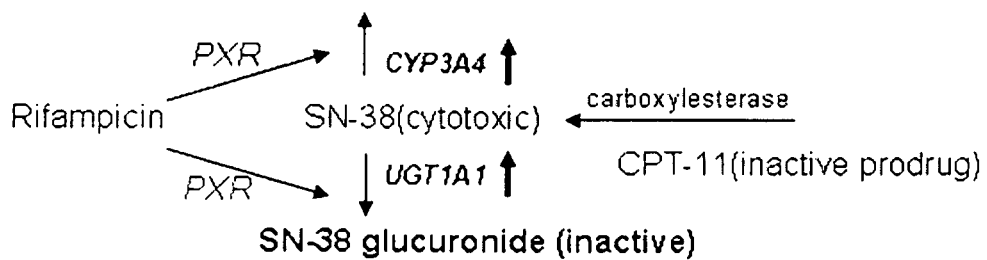
Figure 7C:
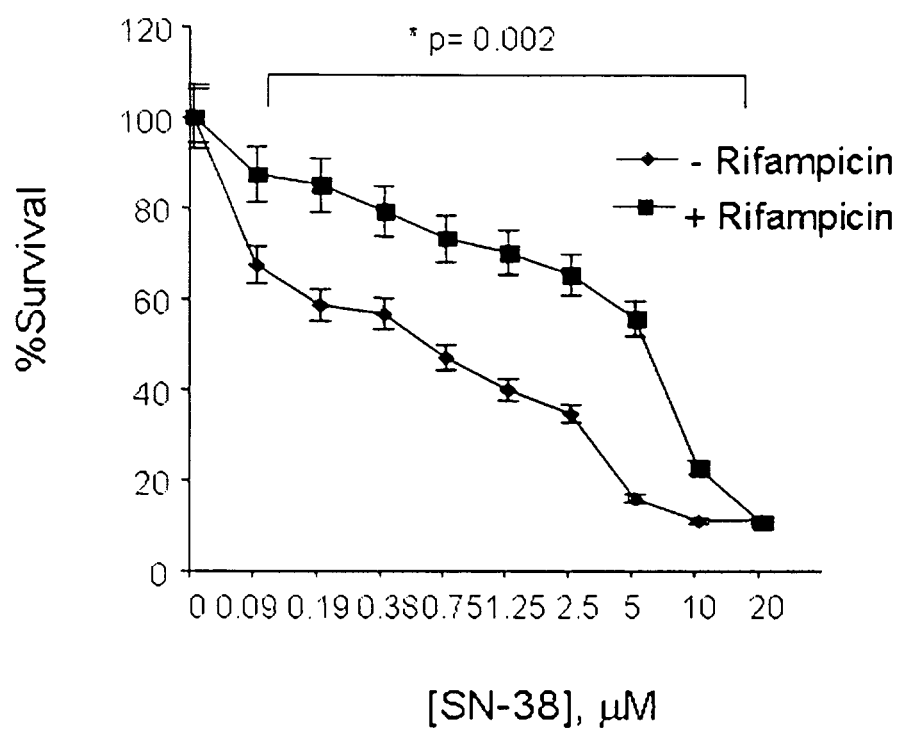

The role of PXR in cancer cell drug resistance has been unclear. In SKOV-3 cells, rifampicin (20 μM) significantly decreased the cytotoxicity of, ixabepilone over a concentration range (0.1-50 μM) (FIG. 7A), of paclitaxel over a concentration range (0.1-10 μM) (FIG. 7B), of SN-38 (active metabolite of CPT-11) over a concentration range (0.05-1.0 μM) (FIG. 7C). The metabolites of ixabepilone, paclitaxel and SN-38 are non-toxic to cells. As an example, this has been shown for the metabolites of paclitaxel (see FIG. 7B(i) and (ii)). Since $IC_{50}$'s have not been reached for ixabepilone in SKOV-3 cells, the resistance to ixabepilone (0.1-50 μM) in the presence of rifampicin is best represented as % increased survival relative to ixabepilone without rifampicin. This averages to ~20% (FIG. 7A). For paclitaxel, the resistance index induced by rifampicin is ~10-fold ($IC_{50}$ with rifampicin (R)/$IC_{50}$ without rifampicin (no R) ~40 μM/4 μM) (FIG. 7B). For SN-38, the resistance index induced by rifampicin is ~17.5 ($IC_{50}$(R)/$IC_{50}$ (no R)~3.5/0.2).

PXR Activation in LS174T Cells Induces Cell Proliferation.

Figure 8A:
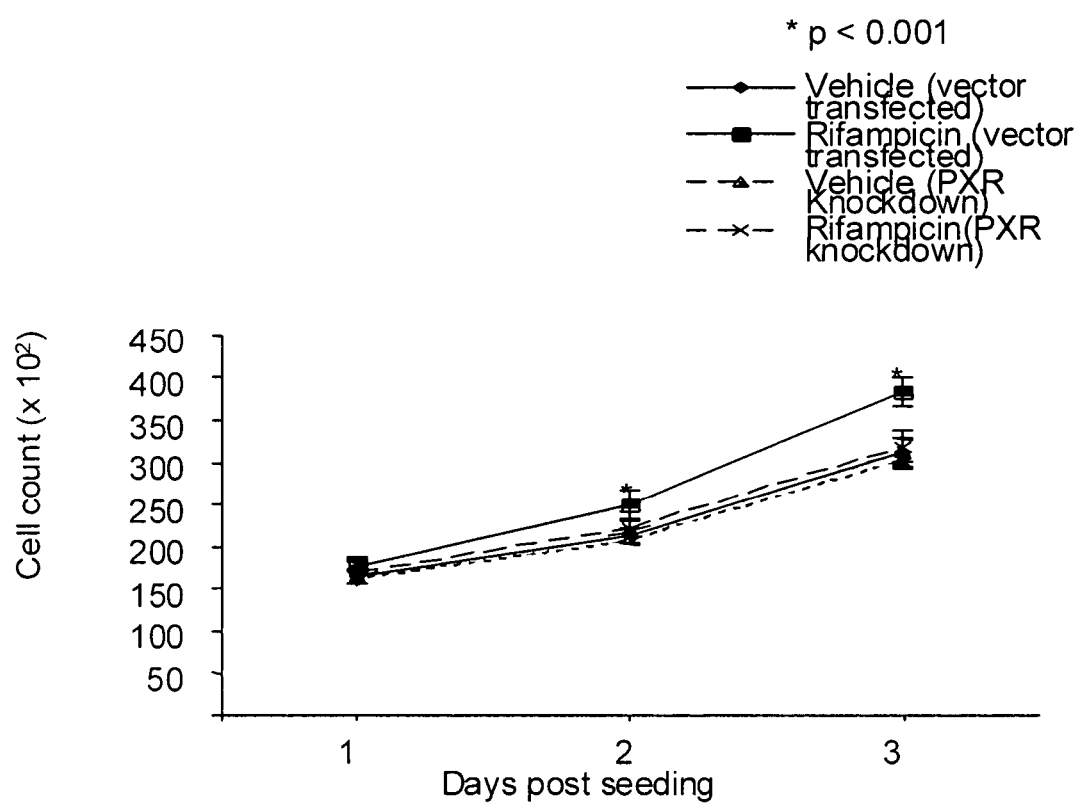
Figure 8B:
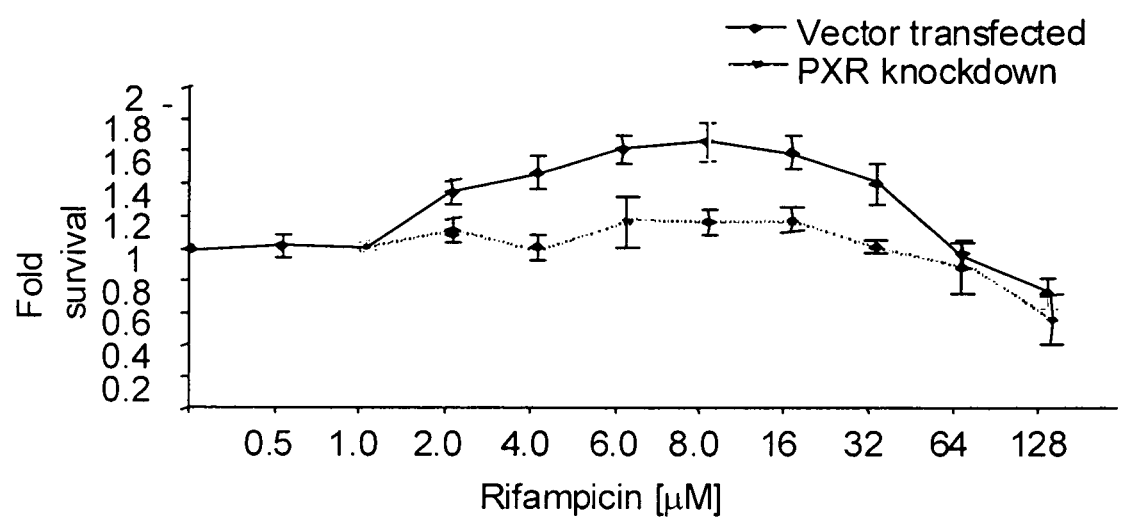
Figure 8D:
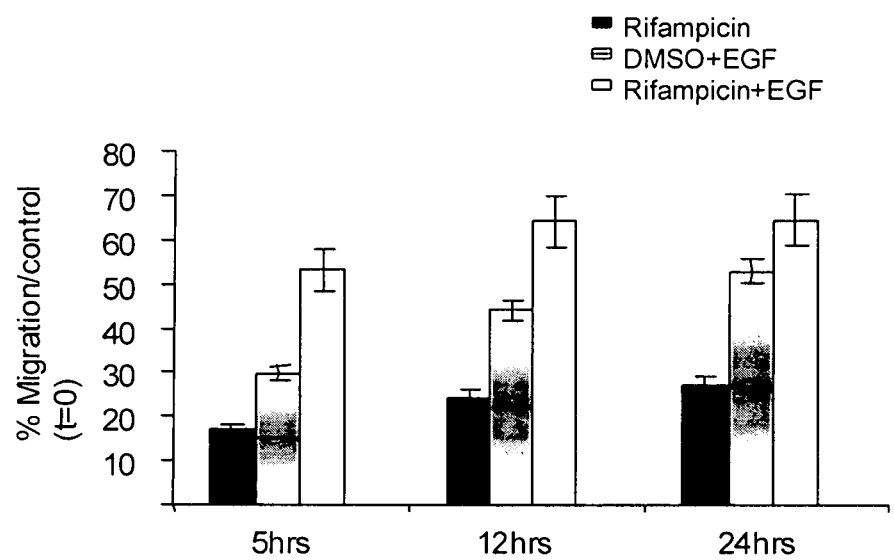

FIG. 8A shows the doubling time of LS174T cells in the presence and absence of the PXR agonist, rifampicin. Vector (Lenti-CMV-GFP) and PXR knockdown (Lenti-CMV-PXR-shRNA-GFP) LS174T cells were seeded into 24-well plates at a density of 17,500 viable cells/well. After seeding, cells were treated with rifampicin or vehicle control as indicated. At 24, 48 and 72 hours, cells were trypsinized and counted using trypan blue staining. Each assay was performed as six replicates and experiments were repeated eight times. The growth rate constants (k=ln 2/g, where ln 2 is the natural log of 2 and "g" is the time in hours taken from the population to double during the exponential phase of growth within 72 hours) for rifampicin treated vector-transfected cells and rifampicin-treated PXR knockdown cells is ~0.02 hr$^{-1}$ and ~0.008 hr$^{-1}$, respectively. * p<0.001, student t test FIG. 8B shows survival of LS174T cells as determined using the MTT assay, in the presence and absence of rifampicin. The data are shown as fold survival (values normalized to vehicle control). Each assay was performed four separate times each in triplicate. LS174T cells were also grown as xenografts in 6-8 week old C57BL/6 mice (n=6 per treatment group; LS174T cells) (FIG. 8C(I)). On day 20, clinically palpable (~15-20 mm$^3$) tumors on each flank were treated with rifampicin (i.p., 3 days/week till day 50). Tumors were measured every other day and plotted in 5-day intervals. On day 50, all animals were sacrificed, and tumors excised and weighed (FIG. 8C(II)). Transwell migration assay was determined at three time points, 5, 12 and 24 hrs in the presence or absence of rifampicin (25 μM) or EGF (5 nM) or both (FIG. 8D). Each assay was performed four separate times each in triplicate. The vehicle control for all experiments was 0.2% DMSO.

Discussion

PXR activation has the potential to interfere with drug therapy in a number of ways. For example, PXR is a key regulator of the permissibility of drugs across the blood-brain barrier (32, 35). PXR activation upregulates p-glycoprotein, as well as other transporters such as MRP2. Since many commonly used anticancer drugs are transported by these efflux pumps, drugs are immediately pumped back into the circulation. Hence, activation of PXR tightens the blood-brain barrier and limits influx of drugs into brain tumors. For patients with primary brain tumors or metastases to the brain, this represents a hurdle for effective therapeutics.

PXR is also a know orphan receptor engaged in drug-drug interaction effects. For example, St. John's Wort, hyperfoin, activates PXR and lowers the therapeutic drug concentrations of CPT-11, a FDA approved drug for the treatment of colon cancer (36). Controlled inhibition of PXR activation would thus preserve inadvertent lowering of beneficial drug concentrations. This would serve to lower initial drug doses for patients and reduce the cost of chemotherapy.

PXR activation in the gut can lower drug bioavailability. Inhibition of PXR in the context of oral drug therapy can improve overall drug availability, and reduce waste and costs associated with therapy.

As shown in the present disclosure, PXR activation induces cell proliferation and multi-drug resistance in ovarian cancer cells. The data regarding PXR mediated induction of drug resistance demonstrates that PXR activation can increase the cytotoxic threshold of cells to chemotherapy. Down-regulation of PXR has been reported to inhibit endometrial cancer cell growth and induce apoptosis (33, 34). As described herein, PXR activation was also shown to induce cell proliferation in colon carcinoma cells.

As described herein, ketoconazole analogs have been developed that antagonize activated PXR yet have reduced cytotoxicity compared with ketoconazole. Accordingly, PXR-inhibiting compounds of the present invention are expected to be useful for improving delivery of chemotherapy to the brain, preserving concentrations of active drugs in chronic therapy, preventing drug-drug interactions during chemotherapy, and inhibiting potential growth and drug resistance of tumors.

REFERENCES (1) Chawla, A., Repa, J. J., Evans, R. M., and Mangelsdorf, D. J. (2001) Nuclear receptors and lipid physiology: opening the X-files. Science 294, 1866-70.
(2) Gronemeyer, H., Gustafsson, J. A., and Laudet, V. (2004) Principles for modulation of the nuclear receptor superfamily. Nat Rev Drug Discov 3, 950-64.
(3) Mangelsdorf, D. J., and Evans, R. M. (1995) The RXR heterodimers and orphan receptors. Cell 83, 841-50.
(4) Mangelsdorf, D. J., Thummel, C., Beato, M., Herrlich, P., Schutz, G., Umesono, K., Blumberg, B., Kastner, P., Mark, M., Chambon, P., and et al. (1995) The nuclear receptor superfamily: the second decade. Cell 83, 835-9.
(5) Ingraham, H. A., and Redinbo, M. R. (2005) Orphan nuclear receptors adopted by crystallography. Curr Opin Struct Biol 15, 708-15.
(6) McDonnell, D. P., Connor, C. E., Wijayaratne, A., Chang, C. Y., and Norris, J. D. (2002) Definition of the molecular and cellular mechanisms underlying the tissue-selective agonist/antagonist activities of selective estrogen receptor modulators. Recent Prog Horm Res 57, 295-316.
(7) Shiau, A. K., Barstad, D., Loria, P. M., Cheng, L., Kushner, P. J., Agard, D. A., and Greene, G. L. (1998) The structural basis of estrogen receptor/coactivator recognition and the antagonism of this interaction by tamoxifen. Cell 95, 927-937.
(8) Kliewer, S. A., Moore, J. T., Wade, L., Staudinger, J. L., Watson, M. A., Jones, S. A., McKee, D. D., Oliver, B. B., Willson, T. M., Zetterstrom, R. H., Perlmann, T., and Lehmann, J. M. (1998) An orphan nuclear receptor activated by pregnanes defines a novel steroid signaling pathway. Cell 92, 73-82.
(9) Fayard, E., Auwerx, J., and Schoonjans, K. (2004) LRH-1: an orphan nuclear receptor involved in development, metabolism and steroidogenesis. Trends Cell Biol 14, 250-60.
(10) Bertilsson, G., Heidrich, J., Svensson, K., Asman, M., Jendeberg, L., Sydow-Backman, M., Ohlsson, R., Postlind, H., Blomquist, P., and Berkenstam, A. (1998) Identification of a human nuclear receptor defines a new signaling pathway for CYP3A induction. Proceedings of the National Academy of Sciences of the United States of America 95, 12208-13.
(11) Wang H, Huang H, Li H, Teotico D G, Sinz M, Baker S D, Staudinger J, Kalpana G, Redinbo M R, Mani S (2007) Activated Pregnenolone X-Receptor Is a Target for Ketoconazole and Its Analogs. Clin Cancer Res 13:2488-2495.
(12) Zhou C, Poulton E-J, Grun F, Bammler T K, Blumberg B, Thummel K E, Eaton D L (2007) The dietary isothiocyanate sulforaphane is an antagonist of the human steroid and xenobiotic nuclear receptor. Mol Pharmacol 71:220-9.
(13) Synold T W, Dussault I, Forman B M (2001) The orphan nuclear receptor SXR coordinately regulates drug metabolism and efflux. Nat Med 7:584-90.
(14) Takeshita A, Taguchi M, Koibuchi N, Ozawa Y (2002) Putative role of the orphan nuclear receptor SXR (steroid and xenobiotic receptor) in the mechanism of CYP3A4 inhibition by xenobiotics. J Biol Chem 277:32453-8.
(15) Huang H, Wang H, Sinz M, Zoeckler M, Staudinger J, Redinbo M R, Teotico D G, Locker J, Kalpana G V, Mani S (2007) Inhibition of drug metabolism by blocking the activation of nuclear receptors by ketoconazole. Oncogene 26: 258-68.

(16) Xue Y C E, Zuercher W J, Willson T M, Collins J L, Redinbo M R. (2007) Crystal structure of the PXR-T1317 complex provides a scaffold to examine the potential for receptor antagonism. Bioorg Med. Chem. 15:2156-66.

(17) Ekins S, Chang C, Mani S, Krasowski M D, Reschly E J, Iyer M, Kholodovch V, Ai Ni, William J W, Sinz M, Swaan P W, Patel R, Bachman K. (2007) Human pregnane x receptor antagonists and agonists define molecular requirements for different binding sites. Mol. Pharmacol. September; 72(3):592-603.

(18) Estébanez-Perpiñá E, Arnold A A, Nguyen P, Rodrigues E D, Mar E, Bateman R, Pallai P, Shokat K M, Baxter J D, Guy R K, Webb P, Fletterick R J (2007) A surface on the androgen receptor that allosterically regulates coactivator binding. Proc Natl Acad Sci USA. October 9; 104(41): 16074-9.

(19) Wu K M, Wang C G, D'Amico M, Lee R J, Albanese C, Pestell, R, Mani S. (2002) Flavopiridol and Trastuzumab Synergistically Inhibit Proliferation of Breast Cancer Cells: Association with Selective Cooperative Inhibition of Cyclin D1 Dependent Kinase and Akt Signaling Pathways. Mol Cancer Ther. 1: 695-706.

(20) Wu K M, Wang C G, D'Amico M, Albanese C, Pestell, R, Mani S. (2005) Flavopiridol synergizes with UCN-01: Role of surviving in reversal of resistance to UCN-01. Invest New Drugs 23: 299-309.

(21) Power E C, Ganellin C R, Benton C H (2006) Partial structures of ketoconazole as modulators of the large conductance calcium-activated potassium channel ($BK_{Ca}$) Bioorganic & Medicinal Chemistry Letters 16: 887-890.

(22) Verras, A.; Alian, A.; de Montellano P R. (2006) Cytochrome P450 active site plasticity: attenuation of imidazole binding in cytochrome P450(cam) by an L244A mutation. Protein Eng Des Sel. 19(11):491-6. Epub 2006 Aug. 30.

(23) Heeres J, Backx, L. J.; Mostmans, J. H.; Van Cutsem, J. (1979) Antimycotic imidazoles. part 4. Synthesis and antifungal activity of ketoconazole, a new potent orally active broad-spectrum antifungal agent. J Med. Chem. 22: 1003-5.

(24) Pelayo Camps, Xavier FarrésMa Luisa García, Joan Ginesta, Jaume Pascual, David Mauleón and Germano Carganico. (1995) Stereoselective synthesis of both enantiomers of ketoconazole from (R)- and (S)-epichlorohydrin Tetrahedron: Asymmetry 6: 283.

(25) Lu D, Zhang H, Koo H, et al. A Fully Human Recombinant IgG-like Bispecific Antibody to Both the Epidermal Growth Factor Receptor and the Insulin-like Growth Factor Receptor for Enhanced Antitumor Activity. JBC 2005; 280:19665-72.

(26) Miki Y, Suzuki T, Kitada K, et al. Expression of the Steroid and Xenobiotic Receptor and Its Possible Target Gene, Organic Anion Transporting Polypeptide-A, in Human Breast Carcinoma. Cancer Res 2006; 66:535-42.

(27) Mitro N, Vargas L, Romeo R, et al. T0901317 is a potent PXR ligand: implications for the biology ascribed to LXR. FEBS Lett 2007; 581:1721-6.

(28) Xue Y, Chao E, Zuercher W J, et al. Crystal structure of the PXR-T1317 complex provides a scaffold to examine the potential for receptor antagonism. Bioorg Med Chem 2007; 15:2156-66.

(29) Watkins R E, Noble S M, Redinbo M R. Structural insights into the promiscuity and function of the human pregnane X receptor. Curr Opin Drug Discov Devel 2002; 5:150-8.

(30) Watkins R E, Maglich J M, Moore L B, et al. 2.1 A crystal structure of human PXR in complex with the St. John's wort compound hyperforin. Biochemistry 2003; 42:1430-8.

(31) Mani S, Huang H, Sundarababu S, et al. Activation of the steroid and xenobiotic receptor (human pregnane X receptor) by nontaxane microtubule-stabilizing agents. Clin Cancer Res. 2005 Sep. 1; 11(17):6359-69.

(32) Bauer B, Hartz A M, Fricker G, et al. Pregnane X receptor up-regulation of P-glycoprotein expression and transport function at the blood-brain barrier. Mol Pharm 2004; 66:413-9.

(33) Masuyama H, Nakatsukasa H, Takamoto N, et al. Downregulation of Pregnane X Receptor Contributes to Cell Growth Inhibition and Apoptosis by Anti-cancer Agents in Endometrial Cancer Cells. Mol. Pharmacol. 2007 October; 72(4):1045-53. Epub 2007 Jul. 17.

(34) Masuyama H, Hiramatsu Y, Kodama, et al. Expression and Potential Roles of Pregnane X Receptor in Endometrial Cancer. J Clin Endo & Metab 2003; 88:4446-54.

(35) Bauer B, Yang X, Hartz A M, Olson E R, Zhao R, Kalvass J C, Pollack G M, Miller D S. In vivo activation of human pregnane X receptor tightens the blood-brain barrier to methadone through P-glycoprotein up-regulation. Mol. Pharmacol. 2006 October; 70(4):1212-9. Epub 2006 Jul. 12.

(36) Mannel M. Drug interactions with St John's wort: mechanisms and clinical implications. Drug Saf. 2004; 27(11):773-97. Review.

---

What is claimed is:

1. A compound having the formula:

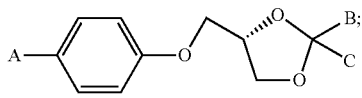

wherein A is

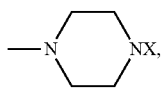

where X is H, CHO, COCH$_3$, CO—OCH$_3$, CO—OC$_2$H$_5$, CONH$_2$, CONHCH$_3$, CONHC$_2$H$_5$, CSNHCH$_3$, CH$_2$CH$_3$, COO—CH$_3$, COO—C$_2$H$_5$, CH$_3$, CH$_2$—CH(CH$_3$)$_2$, CO—NH—(CH$_2$)$_2$CH$_3$, CH(CH$_3$)$_2$, (CH$_2$)$_3$CH$_3$, (CH$_2$)$_2$CH$_3$, SO$_2$CH$_3$, CH$_2$C$_6$H$_5$, or SO$_2$CH$_2$C$_6$H$_5$;

wherein B is methyl, ethyl, propyl, butyl, CH$_2$(CH$_2$)$_n$CH$_2$CH$_3$ where n=0-10, cyclopropyl, cyclobutyl, cyclopentyl, cyclohexyl, cycloheptyl,

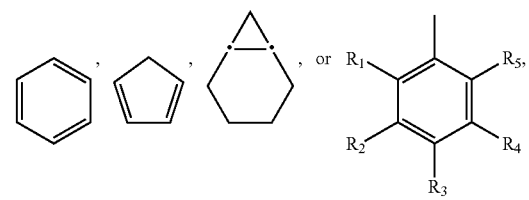

wherein each R$_1$, R$_2$, R$_3$, R$_4$ and R$_5$ is independently H, F, Br, I, OCH$_3$, OC$_2$H$_5$, O-alkyl, SH, S-alkyl, NH$_2$, NH-alkyl, alkyl, or phenyl; and wherein C is ethyl, propyl, butyl, CH$_2$(CH$_2$)$_n$CH$_2$CH$_3$ where n=0-10, cyclopropyl, cyclobutyl, cyclopentyl, cyclohexyl, cycloheptyl,

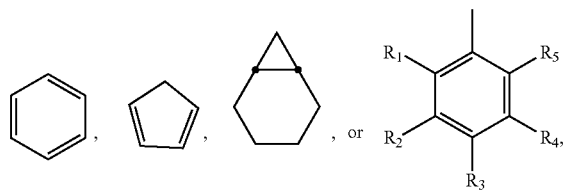

wherein each R$_1$, R$_2$, R$_3$, R$_4$ and R$_5$ is independently H, F, Br, I, OCH$_3$, OC$_2$H$_5$, O-alkyl, SH, S-alkyl, NH$_2$, NH-alkyl, alkyl, or phenyl;

or a pharmaceutically acceptable salt thereof.

2. The compound of claim 1, wherein X is H, CHO or COCH$_3$.

3. The compound of claim 1, wherein A is

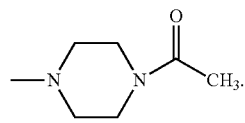

4. The compound of claim 1, wherein B is CH$_3$.

5. The compound of claim 1, wherein C is

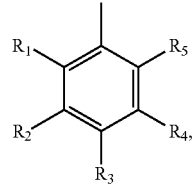

wherein each R$_1$, R$_2$, R$_3$, R$_4$ and R$_5$ is independently H, F, Br or I.

6. The compound of claim 1, wherein C is

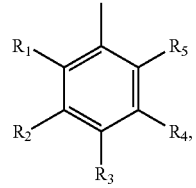

wherein at least two of R$_1$, R$_2$, R$_3$, R$_4$ and R$_5$ are F, Br or I, and the remainder are H.

7. The compound of claim 1, wherein C is

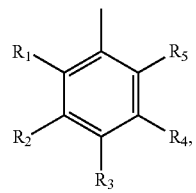

wherein at least R$_3$ is F.

8. The compound of claim 1 having the structure:
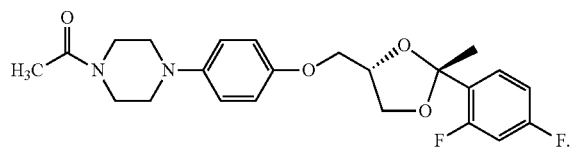 [SMILES: CC(=O)N1CCN(c2ccc(OC[C@H]3CO[C@@](C)(c4ccc(F)cc4F)O3)cc2)CC1]
9. A compound having a structure selected from the group consisting of:
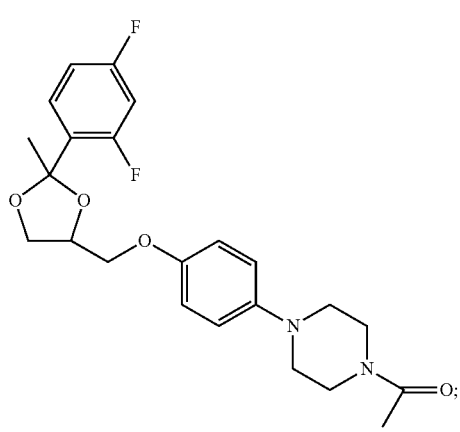
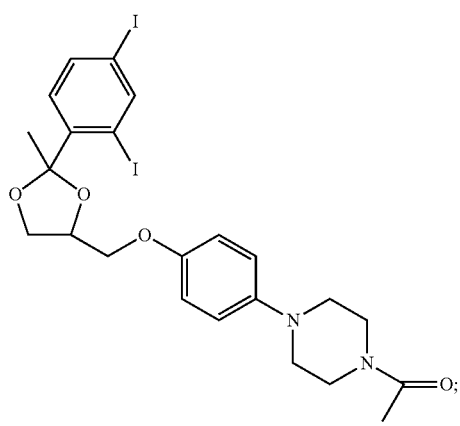
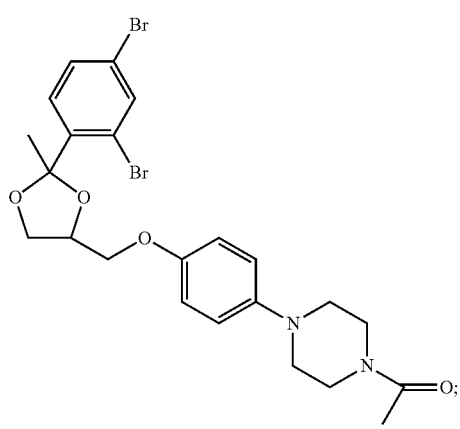 [SMILES: CC(=O)N1CCN(c2ccc(OCC3COC(C)(c4ccc(F)cc4F)O3)cc2)CC1]
-continued
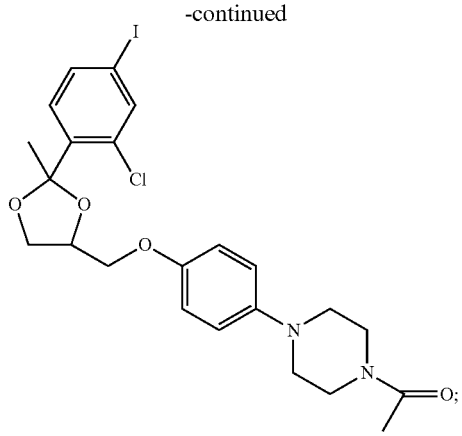
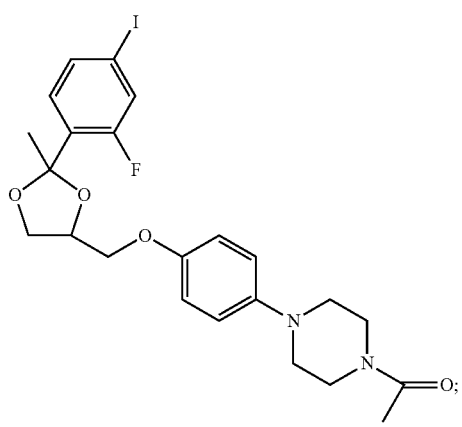
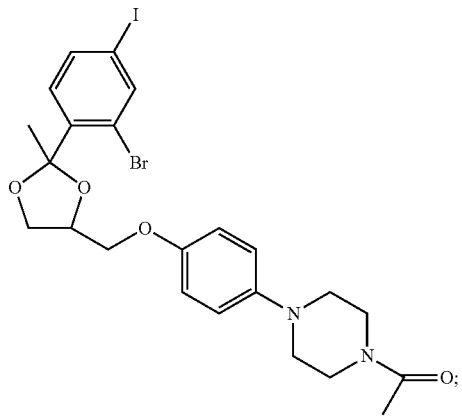

-continued

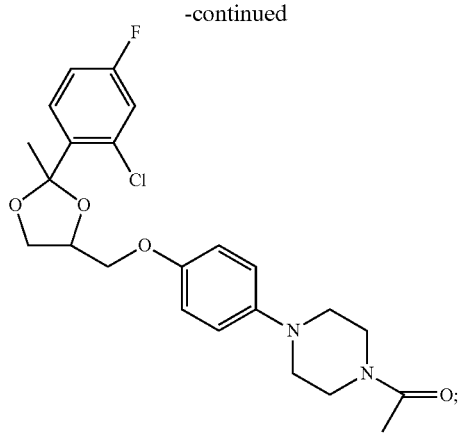

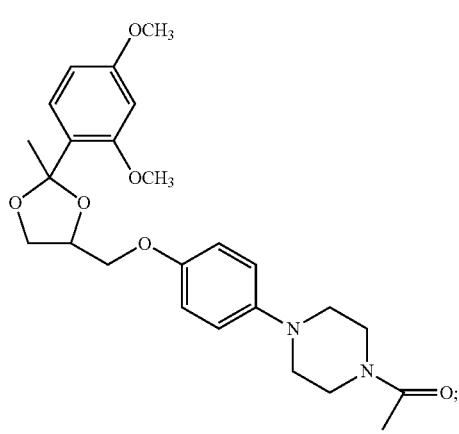

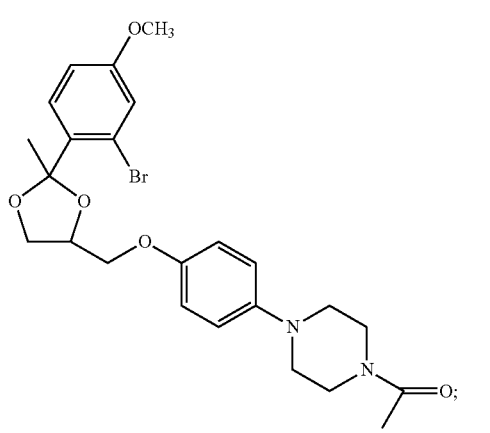
and

-continued

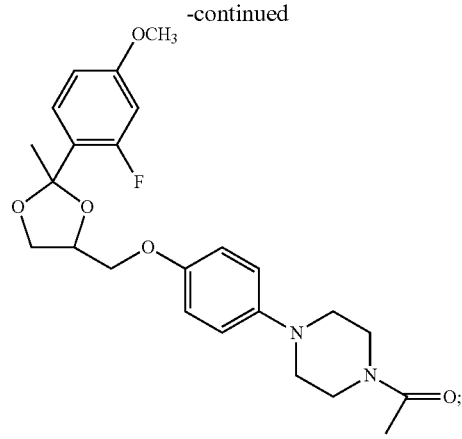

or a pharmaceutically acceptable salt thereof.

10. A pharmaceutical composition for antagonizing the human pregnane X receptor (PXR) comprising the compound of claim 1, and a pharmaceutically acceptable carrier or diluent.

11. The compound of claim 9 having the structure

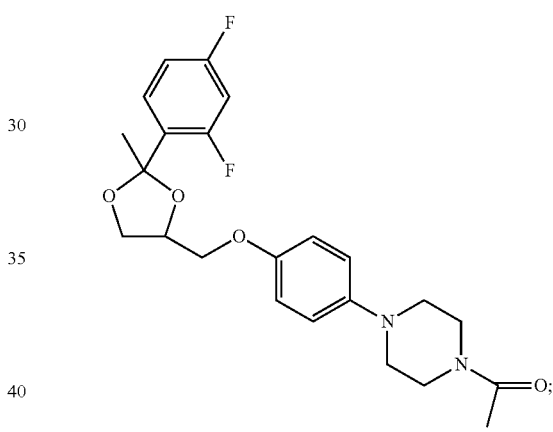

or a pharmaceutically acceptable salt thereof.

12. A pharmaceutical composition for antagonizing the human pregnane X receptor (PXR) comprising the compound of claim 9, and a pharmaceutically acceptable carrier or diluent.

13. A compound having a structure selected from the group consisting of:

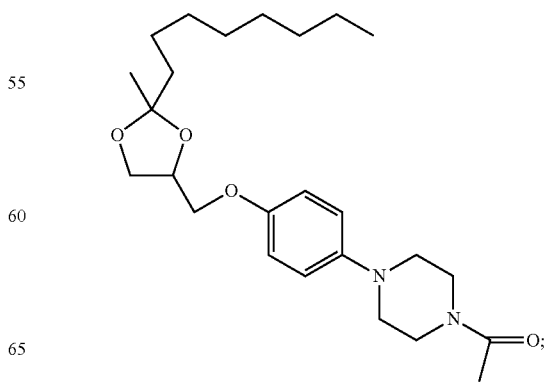

51
-continued
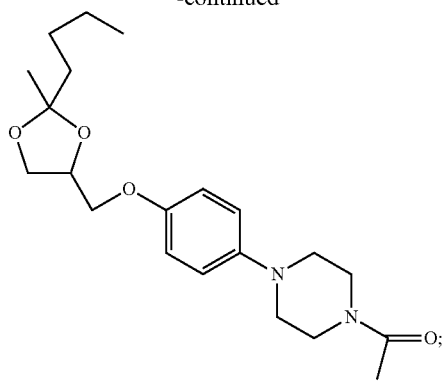
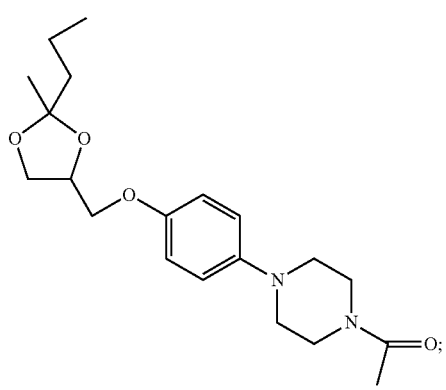
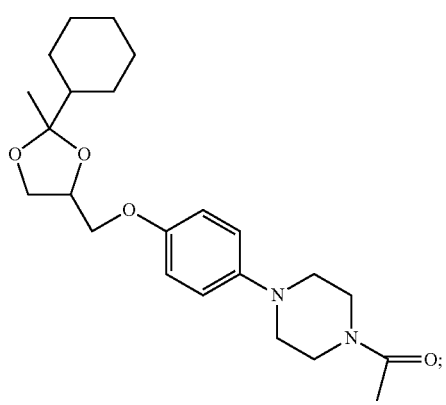
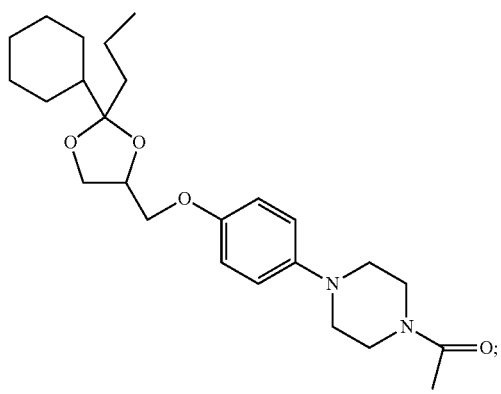
52
-continued
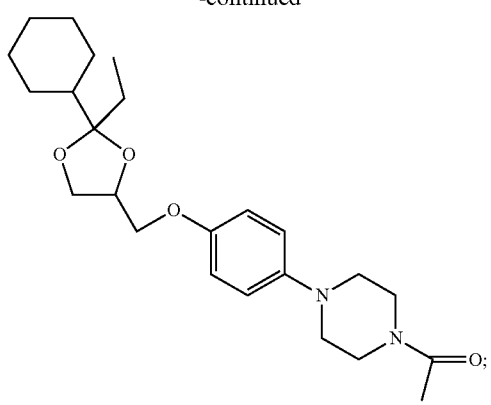
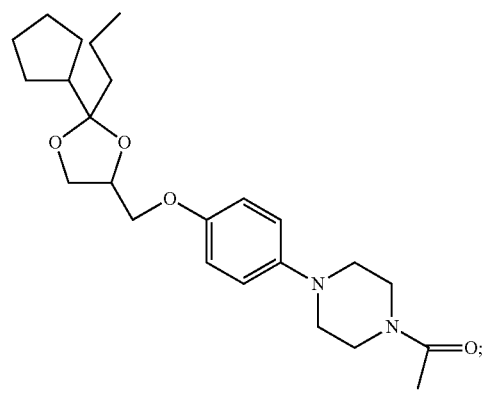
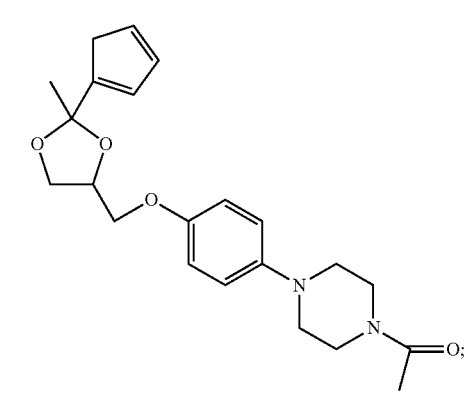

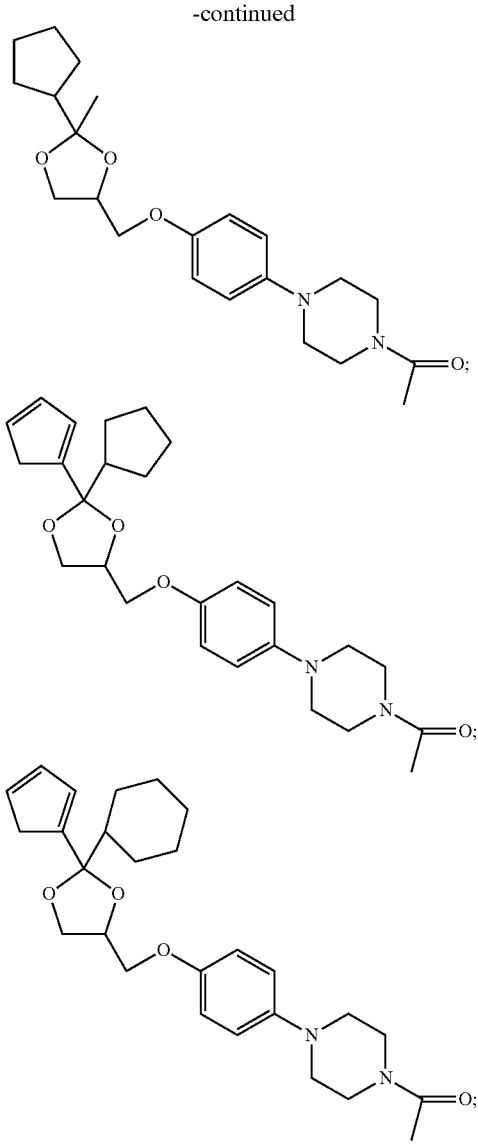
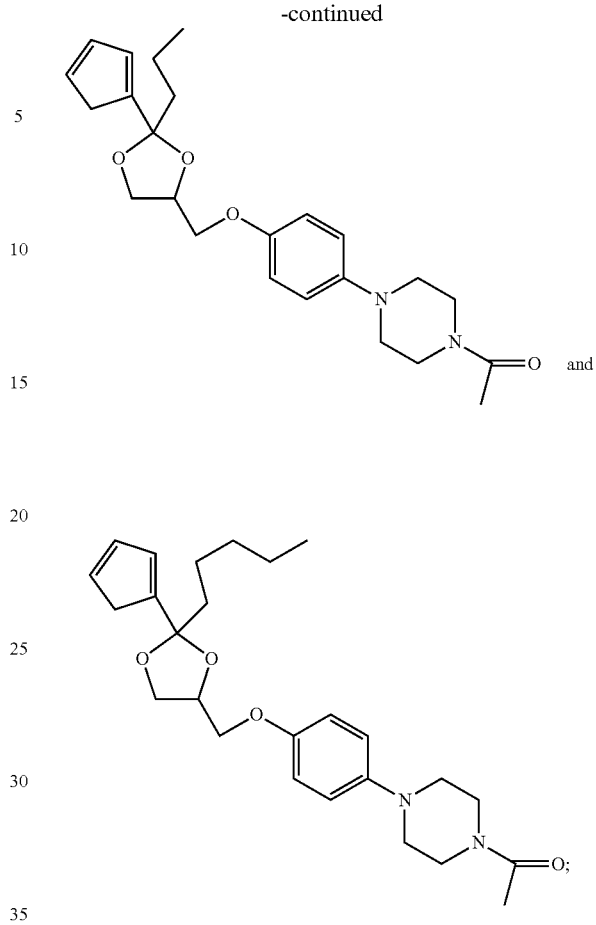
or a pharmaceutically acceptable salt thereof.
14. A pharmaceutical composition for antagonizing the human pregnane X receptor (PXR) comprising the compound of claim 13, and a pharmaceutically acceptable carrier or diluent.
* * * * *

UNITED STATES PATENT AND TRADEMARK OFFICE
CERTIFICATE OF CORRECTION

PATENT NO. : 8,669,260 B2
APPLICATION NO. : 12/735368
DATED : March 11, 2014
INVENTOR(S) : Mani et al.

It is certified that error appears in the above-identified patent and that said Letters Patent is hereby corrected as shown below:

In the specification

Column 1, line 14, insert:

-- STATEMENT OF GOVERNMENT SUPPORT

This invention was made with government support under grant number CA127231 awarded by the National Institutes of Health. The government has certain rights in the invention. --

Signed and Sealed this
Sixteenth Day of August, 2016

Michelle K. Lee
*Director of the United States Patent and Trademark Office*